(12) United States Patent
Woodard et al.

(10) Patent No.: US 11,911,160 B2
(45) Date of Patent: Feb. 27, 2024

(54) AUTOMATED URINE OUTPUT MEASUREMENT SYSTEMS AND METHODS THEREOF

(71) Applicant: C. R. Bard, Inc., Franklin Lakes, NJ (US)

(72) Inventors: Steven P. Woodard, Cupertino, CA (US); Jacob Wolf, Oakland, CA (US); Edward G. Solomon, Menlo Park, CA (US); Russell Ford, Palo Alto, CA (US); William Welch, Sunnyvale, CA (US); Mansour A. Saleki, Kings Beach, CA (US)

(73) Assignee: C. R. Bard, Inc., Franklin Lakes, NJ (US)

( * ) Notice: Subject to any disclaimer, the term of this patent is extended or adjusted under 35 U.S.C. 154(b) by 219 days.

(21) Appl. No.: 17/262,080

(22) PCT Filed: Aug. 8, 2019

(86) PCT No.: PCT/US2019/045787
§ 371 (c)(1),
(2) Date: Jan. 21, 2021

(87) PCT Pub. No.: WO2020/033752
PCT Pub. Date: Feb. 13, 2020

(65) Prior Publication Data
US 2021/0298653 A1    Sep. 30, 2021

Related U.S. Application Data

(60) Provisional application No. 62/717,678, filed on Aug. 10, 2018.

(51) Int. Cl.
*A61B 5/20* (2006.01)
*G16H 10/60* (2018.01)
*A61B 5/00* (2006.01)

(52) U.S. Cl.
CPC ............ *A61B 5/208* (2013.01); *A61B 5/0004* (2013.01); *A61B 5/0022* (2013.01);
(Continued)

(58) Field of Classification Search
CPC .......... A61B 2562/0252; A61B 5/6852; A61B 5/742; A61B 5/746; A61B 5/208;
(Continued)

(56) References Cited

U.S. PATENT DOCUMENTS 3,661,143 A    5/1972    Henkin
3,781,920 A    1/1974    Browne et al.
(Continued)

FOREIGN PATENT DOCUMENTS

CA    2882654 A1    10/2007
CN    2445749 Y     9/2001
(Continued)

OTHER PUBLICATIONS

Bard Medical, Criticore Disposables—Non I.C., 3 pages, www.bardmedical.com/products/patienl-moniloring-.ystems/criticore@-system/criticore@ disposables-non-ic/ Jan. 30, 2015.
(Continued)

*Primary Examiner* — Patrick Fernandes
(74) *Attorney, Agent, or Firm* — Rutan & Tucker LLP

(57) ABSTRACT

An automated urine-output-measurement system can include single-patient equipment and multi-patient equipment. The single-patient equipment can include a urinary catheter and a urine-collection system. The urine-collection system can include drainage tubing and a drainage receptacle. The multi-patient equipment can include a urine monitor. The urine monitor can include a housing having a cavity configured to house the drainage receptacle, a urine-measurement means for measuring urine-output into the drainage receptacle, and an integrated display screen con-
(Continued)

figured to display patient information including measurements of the urine output. A method of the automated urine-output-measurement system can include placing the drainage receptacle in the urine monitor of the automated urine-output-measurement system, and confirming a volume of urine in the drainage receptacle with that indicated on the urine monitor once a patient has produced urine.

20 Claims, 21 Drawing Sheets

(52) U.S. Cl.
CPC ............ *A61B 5/6852* (2013.01); *A61B 5/742* (2013.01); *A61B 5/746* (2013.01); *G16H 10/60* (2018.01); *A61B 2562/0252* (2013.01)

(58) Field of Classification Search
CPC ... A61B 5/0004; A61B 5/0022; A61B 5/0071; A61B 5/201; A61B 5/7267; A61B 10/007; A61B 5/205; G16H 10/60
See application file for complete search history.

(56) References Cited

U.S. PATENT DOCUMENTS

| | | |
|---|---|---|
| 3,851,650 A | 12/1974 | Darling |
| 3,919,455 A | 11/1975 | Sigdell et al. |
| 4,276,889 A | 7/1981 | Kuntz et al. |
| 4,286,590 A | 9/1981 | Murase |
| 4,291,692 A | 9/1981 | Bowman et al. |
| 4,296,749 A | 10/1981 | Pontifex |
| 4,305,405 A | 12/1981 | Meisch |
| 4,312,352 A | 1/1982 | Meisch et al. |
| 4,343,316 A | 8/1982 | Jespersen |
| 4,443,219 A | 4/1984 | Meisch et al. |
| 4,448,207 A | 5/1984 | Parrish |
| 4,509,366 A | 4/1985 | Matsushita et al. |
| 4,532,936 A | 8/1985 | LeVeen et al. |
| 4,658,834 A | 4/1987 | Blankenship et al. |
| 4,723,950 A | 2/1988 | Lee |
| 4,834,706 A | 5/1989 | Beck et al. |
| 4,850,375 A | 7/1989 | Rosenberg |
| 4,889,532 A | 12/1989 | Metz et al. |
| 5,002,541 A | 3/1991 | Conkling et al. |
| 5,409,014 A | 4/1995 | Napoli et al. |
| 5,586,085 A | 12/1996 | Lichte |
| 5,725,515 A | 3/1998 | Propp |
| 5,733,319 A | 3/1998 | Neilson et al. |
| 5,738,656 A | 4/1998 | Wagner |
| 5,747,824 A | 5/1998 | Jung et al. |
| 5,769,087 A | 6/1998 | Westphal et al. |
| 5,807,278 A | 9/1998 | McRae |
| 5,823,972 A | 10/1998 | McRae |
| 5,891,051 A | 4/1999 | Han et al. |
| 5,911,786 A | 6/1999 | Nielsen et al. |
| 6,129,684 A | 10/2000 | Sippel et al. |
| 6,132,407 A | 10/2000 | Genese et al. |
| 6,250,152 B1 | 6/2001 | Klein et al. |
| 6,256,532 B1 | 7/2001 | Cha |
| 6,261,254 B1 | 7/2001 | Baron et al. |
| 6,434,418 B1 | 8/2002 | Neal et al. |
| 6,579,247 B1 | 6/2003 | Abramovitch et al. |
| 6,592,612 B1 | 7/2003 | Samson et al. |
| 6,709,420 B1 | 3/2004 | Lincoln et al. |
| 6,716,200 B2 | 4/2004 | Bracken et al. |
| 7,011,634 B2 | 3/2006 | Paasch et al. |
| 7,161,484 B2 | 1/2007 | Tsoukalis |
| 7,437,945 B1 | 10/2008 | Feller |
| 7,442,754 B2 | 10/2008 | Tepper et al. |
| 7,739,907 B2 | 6/2010 | Boiarski |
| 7,871,385 B2 | 1/2011 | Levinson |
| 7,931,630 B2 | 4/2011 | Nishtala et al. |
| 7,976,533 B2 | 7/2011 | Larsson |
| 7,998,126 B1 | 8/2011 | Fernandez |
| 8,295,933 B2 | 10/2012 | Gerber et al. |
| 8,328,733 B2 | 12/2012 | Forte et al. |
| 8,328,734 B2 | 12/2012 | Salvadori et al. |
| 8,337,476 B2 | 12/2012 | Greenwald et al. |
| 8,374,688 B2 | 2/2013 | Libbus et al. |
| 8,403,884 B2 | 3/2013 | Nishtala |
| 8,471,231 B2 | 6/2013 | Paz |
| 8,663,128 B2 | 3/2014 | Paz et al. |
| 8,773,259 B2 | 7/2014 | Judy et al. |
| 8,790,277 B2 | 7/2014 | Elliott et al. |
| 8,790,320 B2 | 7/2014 | Christensen |
| 8,790,577 B2 | 7/2014 | Mizumoto et al. |
| 8,813,551 B2 | 8/2014 | Boiarski |
| 8,827,924 B2 | 9/2014 | Paz et al. |
| 8,832,558 B2 | 9/2014 | Cardarelli et al. |
| 8,900,196 B2 | 12/2014 | Andino |
| 9,045,887 B2 | 6/2015 | O'Malley |
| 9,050,046 B2 | 6/2015 | Elliott et al. |
| 9,074,920 B2 | 7/2015 | Mendels et al. |
| 9,216,242 B2 | 12/2015 | Nishtala et al. |
| 9,480,821 B2 | 11/2016 | Ciccone et al. |
| 9,592,034 B2 | 3/2017 | Hall et al. |
| 9,642,987 B2 | 5/2017 | Bierman et al. |
| 9,731,097 B2 | 8/2017 | Andino et al. |
| 9,895,095 B2 | 2/2018 | Chen |
| 9,962,516 B2 | 5/2018 | Lampotang et al. |
| 10,182,747 B2 | 1/2019 | Charlez et al. |
| 10,245,008 B2 | 4/2019 | Paige |
| 10,362,981 B2 | 7/2019 | Paz et al. |
| 10,383,606 B1 | 8/2019 | McCord et al. |
| 10,448,875 B2 | 10/2019 | Holt et al. |
| 11,703,365 B2 | 7/2023 | Tourchak et al. |
| 2001/0056226 A1 | 12/2001 | Zodnik et al. |
| 2002/0016719 A1 | 2/2002 | Nemeth et al. |
| 2002/0161314 A1 | 10/2002 | Sarajarvi |
| 2002/0193760 A1 | 12/2002 | Thompson |
| 2003/0000303 A1 | 1/2003 | Livingston et al. |
| 2003/0163183 A1 | 8/2003 | Carson |
| 2003/0163287 A1 | 8/2003 | Vock et al. |
| 2004/0267086 A1 | 12/2004 | Anstadt et al. |
| 2005/0020958 A1 | 1/2005 | Paolini et al. |
| 2005/0065583 A1 | 3/2005 | Voorhees et al. |
| 2005/0172712 A1 | 8/2005 | Nyce |
| 2005/0247121 A1 | 11/2005 | Pelster |
| 2006/0100743 A1 | 5/2006 | Townsend et al. |
| 2007/0010797 A1 | 1/2007 | Nishtala et al. |
| 2007/0145137 A1 | 6/2007 | Mrowiec |
| 2007/0252714 A1 | 11/2007 | Rondoni et al. |
| 2008/0312556 A1 | 12/2008 | Dijkman |
| 2009/0056020 A1 | 3/2009 | Caminade et al. |
| 2009/0099629 A1 | 4/2009 | Carson et al. |
| 2009/0157430 A1 | 6/2009 | Rule et al. |
| 2009/0287170 A1 | 11/2009 | Otto |
| 2009/0315684 A1 | 12/2009 | Sacco et al. |
| 2010/0094204 A1 | 4/2010 | Nishtala |
| 2010/0130949 A1 | 5/2010 | Garcia |
| 2010/0137743 A1 | 6/2010 | Nishtala et al. |
| 2011/0113540 A1 | 5/2011 | Plate et al. |
| 2011/0120219 A1 | 5/2011 | Barlesi et al. |
| 2011/0178425 A1 | 7/2011 | Nishtala et al. |
| 2011/0238042 A1 | 9/2011 | Davis et al. |
| 2011/0251572 A1 | 10/2011 | Nishtala et al. |
| 2011/0263952 A1 | 10/2011 | Bergman et al. |
| 2012/0029408 A1 | 2/2012 | Beaudin |
| 2012/0059286 A1 | 3/2012 | Hastings et al. |
| 2012/0078137 A1 | 3/2012 | Mendels et al. |
| 2012/0078235 A1 | 3/2012 | Martin et al. |
| 2012/0095304 A1 | 4/2012 | Biondi |
| 2012/0109008 A1 | 5/2012 | Charlez et al. |
| 2012/0123233 A1 | 5/2012 | Cohen |
| 2012/0127103 A1 | 5/2012 | Qualey et al. |
| 2012/0226196 A1 | 9/2012 | DiMino et al. |
| 2012/0234434 A1 | 9/2012 | Woodruff et al. |
| 2012/0302917 A1 | 11/2012 | Fitzgerald et al. |
| 2012/0323502 A1 | 12/2012 | Tanoura et al. |
| 2013/0066166 A1 | 3/2013 | Burnett et al. |
| 2013/0109927 A1 | 5/2013 | Menzel |
| 2013/0109928 A1 | 5/2013 | Menzel |

(56) References Cited

U.S. PATENT DOCUMENTS

| | | |
|---|---|---|
| 2013/0131610 A1 | 5/2013 | Dewaele et al. |
| 2013/0218106 A1 | 8/2013 | Coston et al. |
| 2013/0245498 A1 | 9/2013 | Delaney et al. |
| 2013/0267871 A1 | 10/2013 | Delaney et al. |
| 2014/0039348 A1 | 2/2014 | Bullington et al. |
| 2014/0155781 A1 | 6/2014 | Bullington et al. |
| 2014/0155782 A1 | 6/2014 | Bullington et al. |
| 2014/0159921 A1 | 6/2014 | Qualey et al. |
| 2014/0207085 A1 | 7/2014 | Brandt et al. |
| 2014/0243635 A1 | 8/2014 | Arefieg |
| 2014/0335490 A1 | 11/2014 | Baarman et al. |
| 2015/0343173 A1 | 12/2015 | Tobescu et al. |
| 2015/0359522 A1 | 12/2015 | Recht et al. |
| 2015/0362351 A1 | 12/2015 | Joshi et al. |
| 2016/0051176 A1 | 2/2016 | Ramos et al. |
| 2016/0183819 A1 | 6/2016 | Burnett et al. |
| 2017/0100068 A1* | 4/2017 | Kostov ............... A61M 39/28 |
| 2017/0196478 A1 | 7/2017 | Hunter |
| 2017/0202698 A1 | 7/2017 | Zani et al. |
| 2017/0249445 A1 | 8/2017 | Devries et al. |
| 2017/0290540 A1 | 10/2017 | Franco |
| 2017/0291012 A1 | 10/2017 | Iglesias |
| 2017/0307423 A1* | 10/2017 | Pahwa ................ G01G 19/18 |
| 2018/0015251 A1 | 1/2018 | Lampotang et al. |
| 2018/0280236 A1* | 10/2018 | Ludin ................. G01F 23/243 |
| 2018/0344234 A1 | 12/2018 | McKinney et al. |
| 2019/0046102 A1 | 2/2019 | Kushnir et al. |
| 2019/0069830 A1 | 3/2019 | Holt et al. |
| 2019/0126006 A1 | 5/2019 | Rehm et al. |
| 2019/0201596 A1 | 7/2019 | Luxon et al. |
| 2019/0223844 A1 | 7/2019 | Aboagye et al. |
| 2019/0247236 A1 | 8/2019 | Sides et al. |
| 2019/0321588 A1 | 10/2019 | Burnett et al. |
| 2019/0328945 A1 | 10/2019 | Analytis et al. |
| 2019/0358387 A1 | 11/2019 | Elbadry et al. |
| 2019/0365308 A1* | 12/2019 | Laing .................. G01F 23/26 |
| 2019/0381223 A1 | 12/2019 | Culbert et al. |
| 2020/0022637 A1 | 1/2020 | Kurzrock et al. |
| 2020/0085378 A1 | 3/2020 | Burnett et al. |
| 2020/0268303 A1 | 8/2020 | Oliva |
| 2020/0289749 A1 | 9/2020 | Odashima et al. |
| 2021/0077007 A1 | 3/2021 | Jouret et al. |
| 2022/0018692 A1 | 1/2022 | Tourchak et al. |
| 2022/0026001 A1 | 1/2022 | Cheng et al. |
| 2022/0026261 A1 | 1/2022 | Funnell et al. |
| 2022/0192564 A1 | 6/2022 | Kriscovich et al. |
| 2022/0192565 A1 | 6/2022 | Cheng et al. |
| 2022/0192566 A1 | 6/2022 | Cheng et al. |
| 2022/0193375 A1 | 6/2022 | Rehm et al. |
| 2022/0296140 A1 | 9/2022 | Nguyen et al. |
| 2022/0386917 A1 | 12/2022 | Mann et al. |
| 2023/0022547 A1 | 1/2023 | Cho et al. |
| 2023/0025333 A1 | 1/2023 | Patel et al. |
| 2023/0028966 A1 | 1/2023 | Franano |
| 2023/0035669 A1 | 2/2023 | Raja et al. |
| 2023/0040915 A1 | 2/2023 | Compton et al. |
| 2023/0058553 A1 | 2/2023 | Fallows et al. |
| 2023/0060232 A1 | 3/2023 | Patel et al. |
| 2023/0084476 A1 | 3/2023 | Robichaud et al. |

FOREIGN PATENT DOCUMENTS

| | | |
|---|---|---|
| CN | 200951235 Y | 9/2007 |
| CN | 201492414 U | 6/2010 |
| CN | 102647939 A | 8/2012 |
| CN | 109498013 A | 3/2019 |
| CN | 110859636 A | 3/2020 |
| CN | 112426156 A | 3/2021 |
| EP | 0342028 A2 | 11/1989 |
| ES | 2760470 T3 | 5/2020 |
| GB | 2576743 A | 3/2020 |
| JP | S49-75171 A | 7/1974 |
| JP | S54-147066 A | 11/1979 |
| JP | S58-190719 A | 11/1983 |
| JP | S60-219517 A | 11/1985 |
| JP | H02-057240 B2 | 12/1990 |
| JP | H08-271301 A | 10/1996 |
| JP | H10-104041 A | 4/1998 |
| JP | 2007-303982 A | 11/2007 |
| JP | 2008-524618 A | 7/2008 |
| JP | 2009-068959 A | 4/2009 |
| JP | 2010-121950 A | 6/2010 |
| JP | 2010-530978 A | 9/2010 |
| JP | 2012-105947 A | 6/2012 |
| JP | 2012-225790 A | 11/2012 |
| WO | 1981003427 A1 | 12/1981 |
| WO | 2004045410 A1 | 6/2004 |
| WO | 2013013782 A2 | 1/2013 |
| WO | 20130178742 A1 | 12/2013 |
| WO | 2014/043650 A2 | 3/2014 |
| WO | 2014108690 A1 | 7/2014 |
| WO | 2014/135856 A1 | 9/2014 |
| WO | 2014/151068 A2 | 9/2014 |
| WO | 2014145971 A2 | 9/2014 |
| WO | 201511402 A1 | 1/2015 |
| WO | 2015/105916 A1 | 7/2015 |
| WO | WO-2015105916 A1 * | 7/2015 ............. A61B 5/208 |
| WO | 2015/127390 A1 | 8/2015 |
| WO | 2016177901 A1 | 11/2016 |
| WO | 2017/023794 A1 | 2/2017 |
| WO | WO-2017023794 A1 * | 2/2017 ........... A61B 10/007 |
| WO | 2018156624 A1 | 8/2018 |
| WO | 2019066357 A1 | 4/2019 |
| WO | 2019/226697 A1 | 11/2019 |
| WO | 2020154370 A1 | 7/2020 |
| WO | 2022108589 A1 | 5/2022 |
| WO | 2022182794 A1 | 9/2022 |

OTHER PUBLICATIONS

Bard Medical, Criticore Infection Control Disposables, 3 pages, www.bardmedical.com/patienl-monitoring-,ystems/criticore@-system/criticore®-infection-control-disposables/ Jan. 30, 2015.

Bard Medical, Criticore Monitor, 11 pages, www.bardmedical.com/products/patient-monitoring-systems/criticore®-monitor/ Jan. 30, 2015.

Bard Medical, Urine Meiers, 3 pages, www.bardmedical.com/products/urological-drainage/urine-collection/urinemeters/Jan. 30, 2015.

Biometrix, Urimetrix, 4 pages, www.biometrixmedical.com/Products/56/Urimetrix%E2%84%A2 Oct. 29, 2014.

Observe Medical, sippi, 3 pages, www.observemedical.com/products.html Oct. 29, 2014.

PCT/US19/33389 filed May 21, 2019 International Search Report and Written Opinion dated Aug. 2, 2019.

PCT/US2016/044835 filed Jul. 20, 2016 International Search Report and Written Opinion dated Dec. 16, 2016.

U.S. Appl. No. 17/054,493, filed Nov. 10, 2020 Final Office Action dated May 31, 2022.

U.S. Appl. No. 15/748,107, filed Jan. 26, 2018 Final Office Action dated Dec. 23, 2020.

U.S. Appl. No. 15/748,107, filed Jan. 26, 2018 Final Office Action dated Feb. 7, 2022.

U.S. Appl. No. 15/748,107, filed Jan. 26, 2018 Non-Final Office Action dated Sep. 3, 2021.

U.S. Appl. No. 15/748,107, filed Jan. 26, 2018 Non-Final Office Action dated Sep. 4, 2020.

U.S. Appl. No. 17/054,493, filed Nov. 10, 2020 Non-Final Office Action dated Nov. 24, 2021.

PCT/US2019/045787 filed Aug. 8, 2019 International Preliminary Report on Patentability dated Feb. 16, 2021.

PCT/US2019/045787 filed Aug. 8, 2019 International Search Report and Written Opinion dated Oct. 2, 2019.

U.S. Appl. No. 15/748,107, filed Jan. 26, 2018 Notice of Allowance dated Dec. 12, 2022.

U.S. Appl. No. 17/054,493, filed Nov. 10, 2020 Non-Final Office Action dated Jan. 27, 2023.

U.S. Appl. No. 17/026,821, filed May 3, 2021 Non-Final Office Action dated Jan. 10, 2023.

U.S. Appl. No. 17/373,535, filed Jul. 12, 2021 Non-Final Office Action dated Nov. 9, 2022.

(56) References Cited

OTHER PUBLICATIONS

PCT/US20/61367 filed Nov. 19, 2020 International Search Report and Written Opinion dated Feb. 22, 2021.

U.S. Appl. No. 17/373,535, filed Jul. 12, 2021 Notice of Allowance dated Feb. 23, 2023.

U.S. Appl. No. 17/556,907, filed Dec. 20, 2021 Restriction Requirement dated May 12, 2023.

DFree Personal—Consumer Product Brochure, 2019.

DFree Pro Brochure 2019.

Leonhauser, D et al., "Evaluation of electrical impedance tomography for determination of urinary bladder volume: comparison with standard ultrasound methods in healthy volunteers."—BioMed Engr On-line; 17:95; 2018.

Li, R., et al., "Design of a Noninvasive Bladder Urinary vol. Monitoring System Based on Bio-Impedance."—Engineering; vol. 5; pp. 321-325; 2013.

PCT/US2022/017574 filed Feb. 23, 2022 Internation Search Report and Written Opinion dated Jun. 8, 2022.

Reichmuth, M., et al., "A Non-invasive Wearable Bioimpedance System to Wirelessly Monitor Bladder Filling."—Dep. of Health Sciences and Technology—Department of Information Technology and Electrical Engineering ETH Zurich, Zurich, Switzerland—Conference Paper, Mar. 2020.

Schlebusch, T. et al., "Bladder volume estimation from electrical impedance tomography" Physiological Measurement, Institute of Physics, Bristol, GB. vol. 35 No. 9 Aug. 20, 2014. (Aug. 20, 2014).

SECA product catalog, https://US.secashop.com/products/seca-mbca/seca-mbca-514/5141321139, last accessed Sep. 11, 2020.

U.S. Appl. No. 17/306,821, filed May 3, 2021 Final Office Action dated Jul. 19, 2023.

U.S. Appl. No. 17/556,907, filed Dec. 20, 2021 Non-Final Office Action dated Aug. 17, 2023.

U.S. Appl. No. 17/054,493, filed Nov. 10, 2020 Final Office Action dated Oct. 4, 2023.

U.S. Appl. No. 17/306,821, filed May 3, 2021 Advisory Action dated Oct. 3, 2023.

U.S. Appl. No. 17/373,546, filed Jul. 12, 2021 Non-Final Office Action dated Nov. 1, 2023.

\* cited by examiner

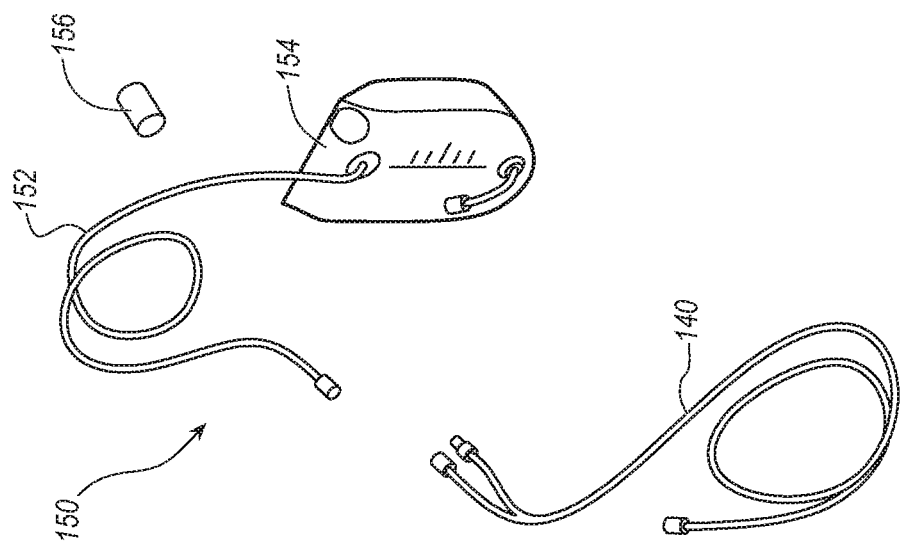
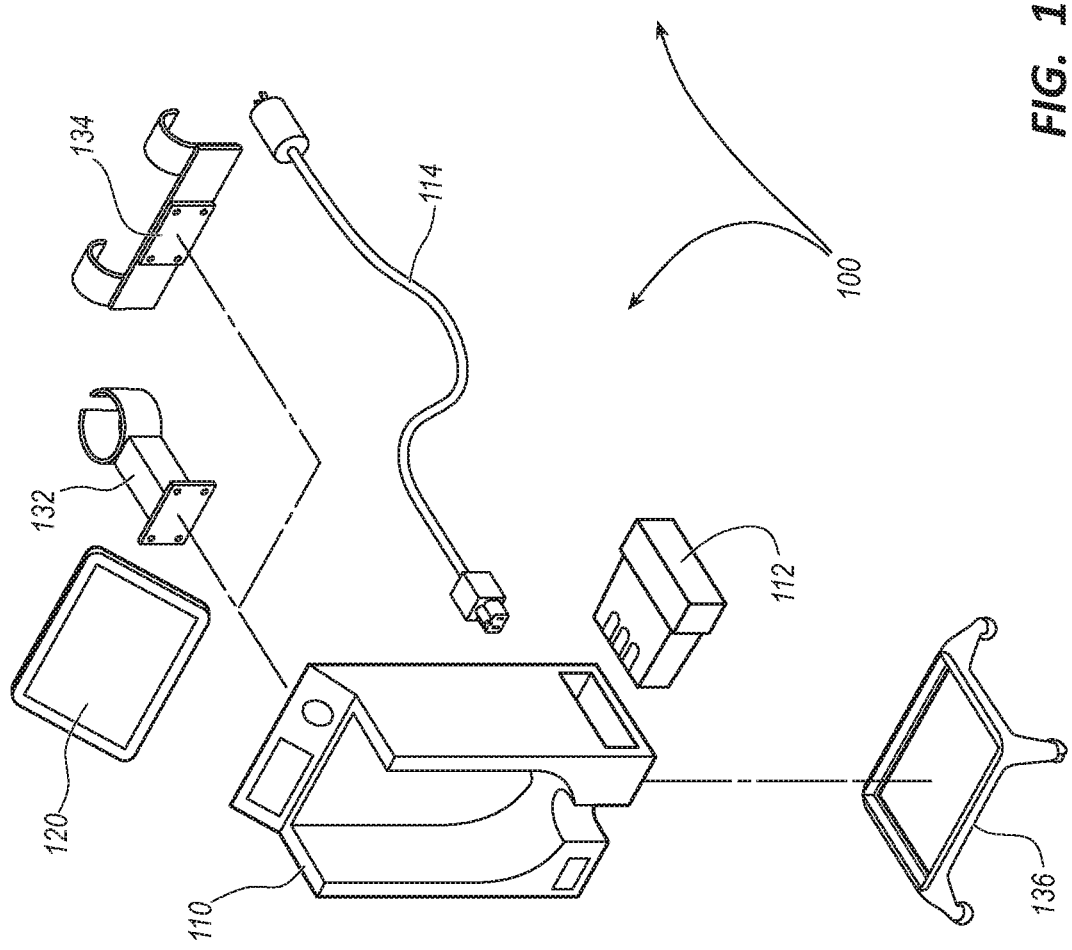
FIG. 1

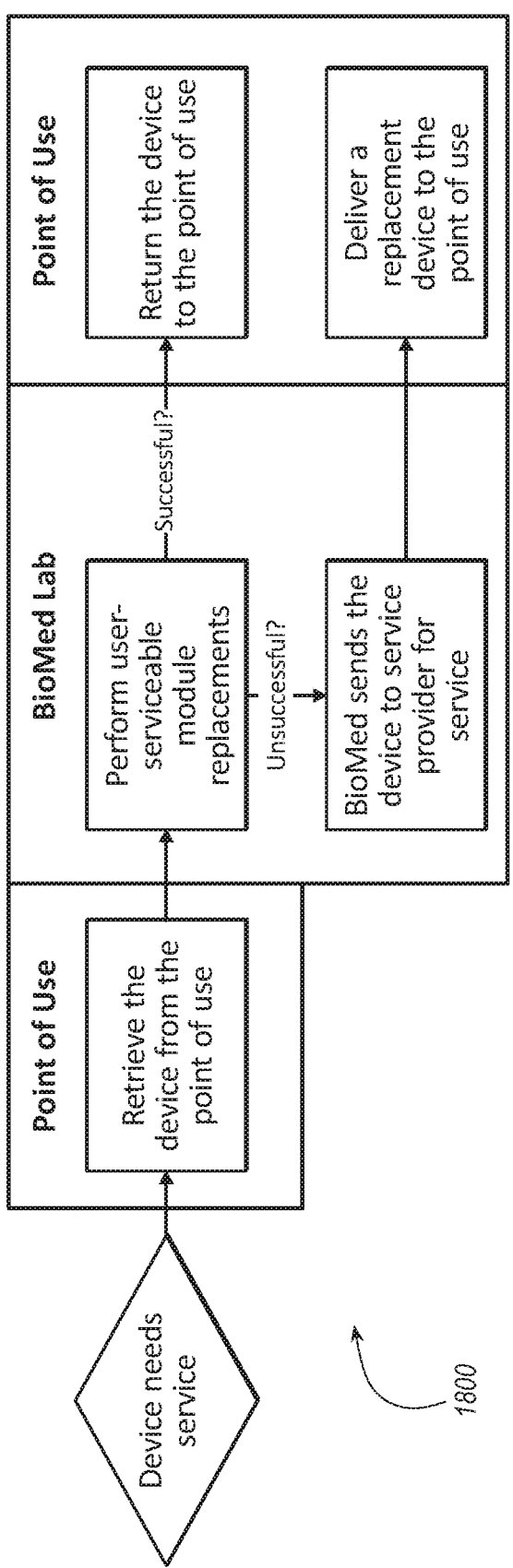
FIG. 18
FIG. 19
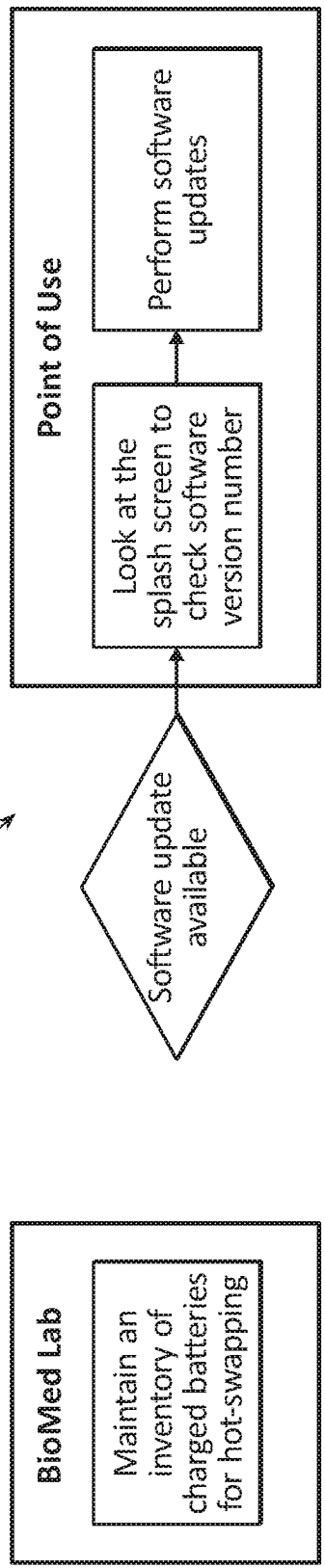
FIG. 20

AUTOMATED URINE OUTPUT MEASUREMENT SYSTEMS AND METHODS THEREOF

This application is a U.S. national stage application of International Application No. PCT/US2019/045787, filed Aug. 8, 2019, which claims the benefit of priority to U.S. Provisional Application No. 62/717,678, filed Aug. 10, 2018, each of which is incorporated by reference in its entirety into this application.

BACKGROUND

Urine-output measurements are used to determine fluid balances and, therefore, fluid imbalances, of patients in, for example, intensive care units ("ICUs"). Currently, urine-output measurements are manually performed, but such measurements can be inaccurate or untimely. In addition, manually performed urine-output measurements can go undocumented—if such measurements are taken at all. As such, manually performed urine-output measurements can lead to erroneous information, which can, in turn, lead to inferior treatment decisions based on the erroneous information. Accurate, timely, and consistent urine-output measurements are needed for better treatment decisions. Furthermore, integration of urine-output measurements into electronic medical records can further improve treatment decisions by improving related workflows.

Disclosed herein are automated urine-output-measurement systems and methods thereof that address at least the foregoing.

SUMMARY

Disclosed herein is an automated urine-output-measurement system including, in some embodiments, single-patient equipment and multi-patient equipment. The single-patient equipment includes a urinary catheter and a urine-collection system. The urine-collection system includes drainage tubing and a drainage receptacle. The multi-patient equipment includes a urine monitor. The urine monitor includes a housing having a cavity configured to house the drainage receptacle; a urine-measurement means for measuring urine-output into the drainage receptacle; and an integrated display screen configured to display patient information including measurements of the urine output.

In some embodiments, the urine-measurement means is a load cell for weight-based urine-output measurements.

In some embodiments, the load cell is a tension load cell located within the housing of the urine monitor. The load cell is coupled to a load-bearing hook located in a back of the cavity such that a load of the drainage receptacle is applied to the load cell while the drainage receptacle hangs from the load-bearing hook.

In some embodiments, the load cell is a compression load cell located in a bottom of the cavity such that a load of the drainage receptacle is applied to the load cell while the drainage receptacle sits on the load cell.

In some embodiments, the urine-measurement means is an in-line flow meter for volume-based urine-output measurements.

In some embodiments, the urine-measurement means is a contactless ultrasonic liquid-level sensor for volume-based urine-output measurements from above the drainage receptacle.

In some embodiments, the urine-measurement means is a contactless optical liquid-level sensor for volume-based urine-output measurements from a side of the drainage receptacle.

In some embodiments, the urine monitor further includes a radiofrequency identification ("RFID")-unit reader-writer configured to identify a presence of an RFID unit integrated into the urine-collection system, read data from the RFID unit, and write data to the RFID unit.

In some embodiments, the RFID unit is a bead around a length of the drainage tubing adjacent the drainage receptacle.

In some embodiments, the housing of the urine monitor has an RFID-unit receptacle including the RFID-unit reader-writer therein or thereabout. The RFID-unit receptacle is configured to retain the drainage tubing by way of the RFID unit.

In some embodiments, the urine monitor further includes lighting features configured to indicate a state of the urine monitor, indicate positive placement of the urine-collection system or a portion thereof, illuminate the drainage receptacle, indicate a urine-urine monitor alert, indicate a patient alert, or a combination thereof.

In some embodiments, the urine monitor further includes an embedded system including a microcontroller, a graphics controller, and one or more wireless communication modules. The microcontroller is configured to process urine-measurement data corresponding to the urine output into the drainage receptacle. The graphics controller is configured to render on the integrated display screen the patient information including the measurements of the urine output. The one or more wireless communication modules are configured to wirelessly communicate the patient information including the urine output to a companion wireless device when paired therewith.

In some embodiments, the multi-patient equipment further includes a companion tablet computer configured to wirelessly communicate with the urine monitor and one or more networked computers. As an intermediate between the urine monitor and the one or more networked computers, the companion tablet computer is configured to update electronic medical records with the patient information including the urine output or retrieve historical patient information from the electronic medical records.

In some embodiments, the multi-patient equipment further includes one or more rechargeable batteries configured to power the urine monitor.

In some embodiments, the multi-patient equipment further includes a pole mount, a bed-rail mount, or a floor stand. The housing of the urine monitor has mounting interfaces to support the pole mount, the bed-rail mount, and the floor stand.

In some embodiments, the multi-patient equipment further includes a urine-clearing device for clearing urine from the drainage tubing.

Disclosed herein is an automated urine-output-measurement system including, in some embodiments, single-patient equipment and multi-patient equipment. The single-patient equipment includes a urinary catheter and a urine-collection system. The urine-collection system includes drainage tubing, a drainage bag, and an optional RFID-bead around a length of the drainage tubing adjacent the drainage bag. The multi-patient equipment includes a urine monitor and a companion tablet computer. The urine monitor includes a housing, a tension load cell located within the housing, an RFID-bead reader-writer, and an integrated display screen. The housing has a cavity configured to house the drainage bag. The housing also has an RFID-bead receptacle configured to retain the drainage tubing by the RFID bead when the RFID bead is present. The tension load cell is located within the housing. The load cell is coupled to a load-bearing hook located in a back of the cavity configured to measure urine output into the drainage bag by applying a load of the drainage bag to the load cell while the drainage bag hangs from the load-bearing hook. The RFID-bead reader-writer is configured to identify a presence of the RFID bead, read patient information from the RFID bead, and write patient information to the RFID bead. The integrated display screen is configured to display the patient information including measurements of the urine output. The companion tablet computer is configured to wirelessly communicate with the urine monitor and one or more networked computers. As an intermediate between the urine monitor and the one or more networked computers, the companion tablet computer is configured to update electronic medical records with the patient information including the urine output or retrieve historical patient information from the electronic medical records.

In some embodiments, the urine monitor further includes an embedded system including a microcontroller, a graphics controller, and one or more wireless communication modules. The microcontroller is configured to process urine-measurement data corresponding to the urine output into the drainage receptacle. The graphics controller is configured to render on the integrated display screen the patient information including the measurements of the urine output. The one or more wireless communication modules are configured to wirelessly communicate the patient information including the urine output to a companion wireless device when paired therewith.

Also disclosed herein is a method of an automated urine-output-measurement system including, in some embodiments, inserting a urinary catheter into a patient if not already inserted into the patient; attaching an RFID unit to drainage tubing of a urine-collection system connected to the urinary catheter if the RFID unit is not already attached to the drainage tubing; associating the RFID unit with the patient in a graphical user interface ("GUI") on an integrated display screen of a urine monitor; placing a drainage bag of the urine-collection system in the urine monitor of the automated urine-output-measurement system; and confirming a volume of urine in the drainage bag with that indicated on the urine monitor once the patient has produced urine.

In some embodiments, the methods further includes removing the drainage bag from the urine monitor; turning the patient in a hospital bed or transporting the patient to another hospital bed; and entering in the GUI on the integrated display screen of the urine monitor or another urine monitor operable to read the RFID unit an amount of the urine drained from the drainage bag while the drainage bag was removed from the urine monitor.

These and other features of the concepts provided herein will become more apparent to those of skill in the art in view of the accompanying drawings and following description, which disclose particular embodiments of such concepts in greater detail.

DRAWINGS

FIG. 1 illustrates an automated urine-output-measurement system in accordance with some embodiments.

FIG. 18 illustrates a method for servicing a urine monitor of an automated urine-output-measurement system when the urine monitor needs service in accordance with some embodiments.

FIG. 19 illustrates a method for hot-swapping a battery in a urine monitor of an automated urine-output-measurement system when the battery is low in accordance with some embodiments.

FIG. 20 illustrates a method for updating software in a urine monitor of an automated urine-output-measurement system when a software update is available in accordance with some embodiments.

DESCRIPTION

Figure 2:
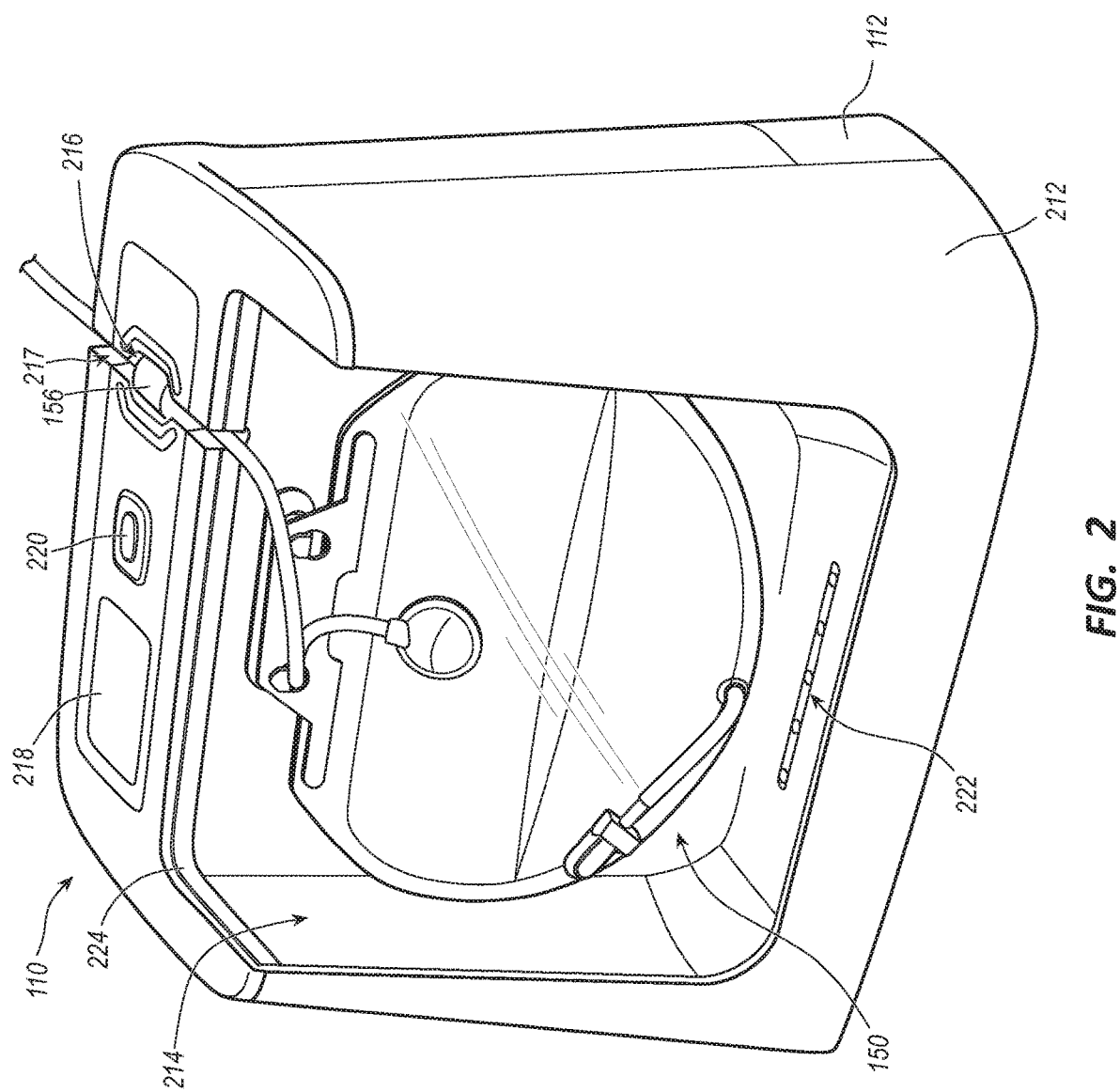
FIG. 2 illustrates a urine monitor and a urine-collection system of the automated urine-output-measurement system in accordance with some embodiments.

Before some particular embodiments are disclosed in greater detail, it should be understood that the particular embodiments disclosed herein do not limit the scope of the concepts provided herein. It should also be understood that a particular embodiment disclosed herein can have features that can be readily separated from the particular embodiment and optionally combined with or substituted for features of any of a number of other embodiments disclosed herein.

Regarding terms used herein, it should also be understood the terms are for the purpose of describing some particular embodiments, and the terms do not limit the scope of the concepts provided herein. Ordinal numbers (e.g., first, second, third, etc.) are generally used to distinguish or identify different features or steps in a group of features or steps, and do not supply a serial or numerical limitation. For example, "first," "second," and "third" features or steps need not necessarily appear in that order, and the particular embodiments including such features or steps need not necessarily be limited to the three features or steps. Labels such as "left," "right," "front," "back," "top," "bottom," "proximal," "distal," and the like are used for convenience and are not intended to imply, for example, any particular fixed location, orientation, or direction. Instead, such labels are used to reflect, for example, relative location, orientation, or directions. Singular forms of "a," "an," and "the" include plural references unless the context clearly dictates otherwise.

Unless defined otherwise, all technical and scientific terms used herein have the same meaning as commonly understood by those of ordinary skill in the art.

Urine-output measurements are used to determine fluid balances and, therefore, fluid imbalances, of patients in, for example, intensive care units ("ICUs"). Currently, urine-output measurements are manually performed, but such measurements can be inaccurate or untimely. In addition, manually performed urine-output measurements can go undocumented—if such measurements are taken at all. As such, manually performed urine-output measurements can lead to erroneous information, which can, in turn, lead to inferior treatment decisions based on the erroneous information. Accurate, timely, and consistent urine-output measurements are needed for better treatment decisions. Furthermore, integration of urine-output measurements into electronic medical records can further improve treatment decisions by improving related workflows.

Disclosed herein are automated urine-output-measurement systems and methods thereof that address at least the foregoing.

Automated Urine-Output-Measurement System

FIG. 1 illustrates an automated urine-output-measurement system 100 in accordance with some embodiments.

As shown, the automated urine-output-measurement system 100 can include capital equipment (e.g., long-term multi-patient equipment) and disposable equipment (e.g., short-term single-patient equipment).

The capital equipment can include a urine monitor 110, one or more rechargeable batteries 112, and a medical-grade power cable 114. The urine monitor 110 can be powered by either the one or more rechargeable batteries 112 or the power cable 114. At any time the one or more batteries 112 are not fully charged, the power cable 114 can be used to simultaneously power the urine monitor 110 and charge the one or more batteries 112 from a general-purpose alternating-current ("AC") electrical power supply. As an alternative to charging the one or more rechargeable batteries 112 in the monitor 110, the capital equipment can further include an external battery-charging device (not shown) configured to charge the one or more rechargeable batteries 112. The urine monitor 110, the external battery-charging device, and the one or more rechargeable batteries 112 are configured such that the one or more batteries 112 can be swapped between the urine monitor 110 and the external battery-charging device with without tools.

The capital equipment can further include a companion wireless device 120 and one or more mounts selected from intravenous ("IV")-pole mount 132, a bed-rail mount 134, and a floor mount or floor stand 136. The urine monitor 110 can be configured to be mounted on any mount of the IV-pole mount 132, the bed-rail mount 134, or the floor stand 136. The bed-rail mount 134 is configured to accommodate either side rail of a hospital bed, thereby enabling the urine monitor 110 to be easily moved from one side of the hospital bed to the other side of the hospital bed to accommodate patient orientation in the hospital bed. The floor stand 136 can have wheels configured to provide mobility to the urine monitor 110 when mounted to the floor stand 136, thereby enabling a patient to move around a hospital or clinic while the urine monitor 110 is being used by the patient.

The disposable equipment can include a urinary catheter 140 (e.g., a Foley catheter), a urine-collection system 150, and an RFID unit 156. The urine-collection system 150 can include drainage tubing 152 for draining urine from the urinary catheter and a drainage receptacle 154 such as a drainage bag, a drainage cassette, or a combination thereof for collecting the urine. The urine-collection system 150 is a fail-safe system in that it is configured to avoid blocking urine flow. In addition, the urine-collection system 150 is configured to maintain any collected urine so as not to compromise measurement accuracy.

While the urine-collection system 150 includes several complementary features to the urine monitor 110, the urine-collection system 150 can be used apart from the urine monitor 110 and a remainder of the capital equipment of the automated urine-output-measurement system 100. This is advantageous in that the urine-collection system 150 can remain with the patient if the patient needs to be moved to another location (e.g., hospital or hospital room) and subsequently transferred to a different set of the capital equipment of the automated urine-output-measurement system 100 or moved to another location lacking the capital equipment of the automated urine-output-measurement system 100. However, using the urine-collection system 150 apart from the remainder of the capital equipment of the automated urine-output-measurement system 100 precludes the advantages of the automated urine-output-measurement system 100 set forth herein.

The disposable equipment can further include a residual urine-clearing means for clearing residual urine from the drainage tubing 152 such as from a drainage port thereof. (See the urine-clearing device 1300 of FIGS. 13-15.)

Urine Monitors

Figure 3:
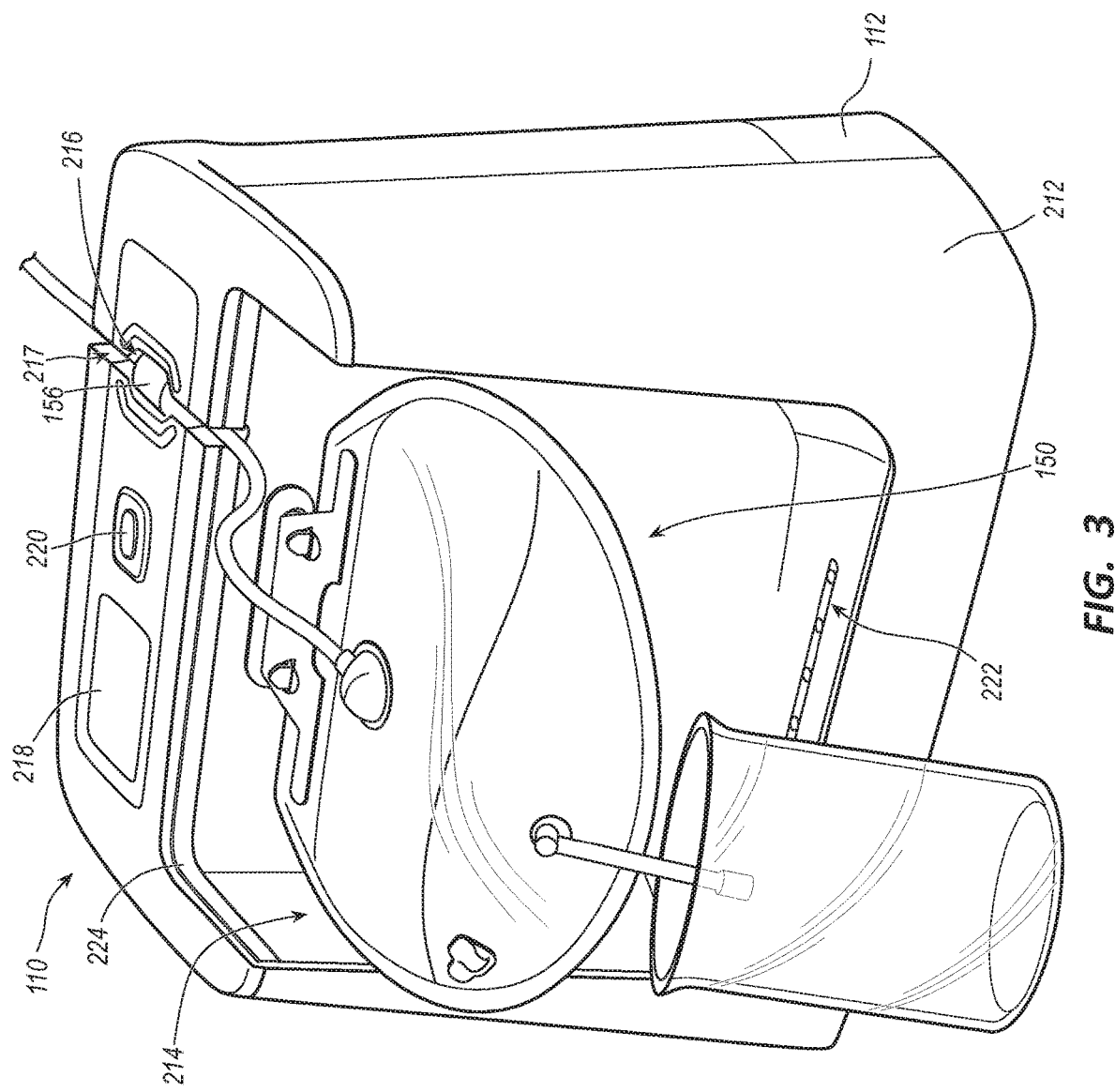
FIG. 3 illustrates the urine monitor and the urine-collection system of the automated urine-output-measurement system in accordance with some embodiments.
Figure 4:
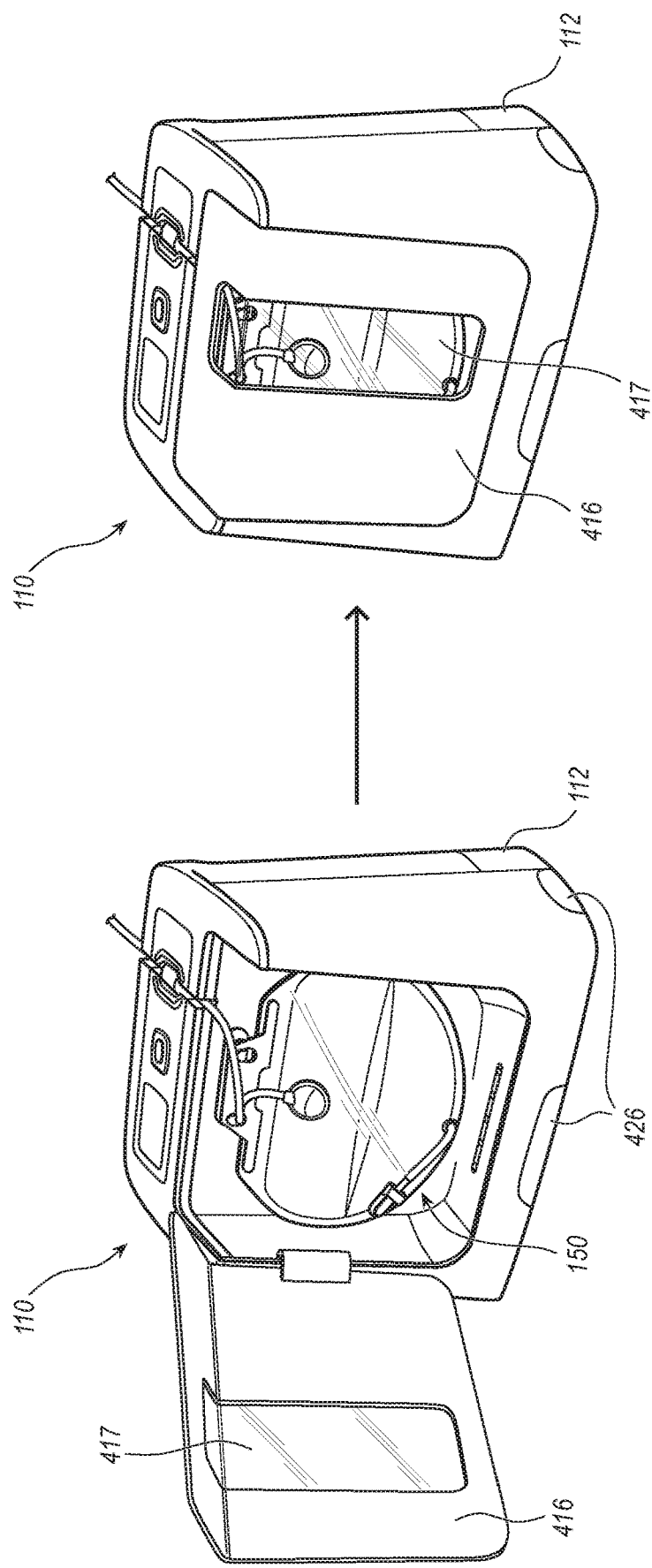
FIG. 4 illustrates the urine monitor and the urine-collection system of the automated urine-output-measurement system in accordance with some embodiments.

FIGS. 2-4 illustrate the urine monitor 110 and the urine-collection system 150 of the automated urine-output-measurement system 100 in accordance with some embodiments.

As shown, the urine monitor 110 can include a housing 212 having a cavity 214 configured to house the drainage receptacle 154. The cavity 214 in the housing 212 is configured to contain the drainage receptacle 154 without obstructing observation of any urine in the drainage receptacle 154 while in use. That said, the urine monitor 110 can further include a door 416 with an optional window 417 to at least partially conceal the drainage receptacle 154 and any urine therein. Even without the door 416, the cavity 214 of the housing 212 is configured to keep the drainage receptacle 154 off potential urine sample-contaminating surfaces such as the floor—particularly when the urine monitor 110 is mounted on the floor mount 136 or an IV pole by way of the IV-pole mount 132.

The housing 212 of the urine monitor 110 can further include an RFID-unit receptacle 216 configured to retain the drainage tubing 152 by way of the RFID unit 156 set forth in more detail below.

While not shown, the housing 212 of the urine monitor 110 can further include a battery compartment configured to accept the one or more batteries 112, a receptacle configured to accept a plug of the power cable 114, and mounting interfaces configured to support the pole mount 132, the bed-rail mount 134, and the floor stand 136.

The urine monitor 110 can further include a user interface including an integrated display screen 218 configured to display patient information including measurements of urine output and—in embodiments in which the integrated display screen 218 is not a touchscreen—a keypad 220 configured for navigating through one or more menus displayed on the integrated display screen 218.

The integrated display screen 218 can be configured with a basic or minimal GUI. The GUI can be configured to convey information such as urine-drainage parameters or summaries thereof. The GUI can be further configured to provide one or more status alerts such as a status of the urine monitor 110 (e.g., a fault alert) or a status of a patient (e.g., a health alert) being monitored by the urine monitor 110. Certain graphical elements of the GUI can be configured to be visible from a distance of at least 10 feet for conveying the foregoing information or providing the foregoing one or more status alerts.

The user interface of the urine monitor 110 can further include visual features produced by, for example, light-emitting diodes ("LEDs") configured to visually indicate a state of the urine monitor 110 (e.g., an "on" state of the urine monitor 110, an active monitoring state of the urine monitor 110, etc.), indicate positive placement of the urine-collection system 150 in the cavity 214 or the RFID unit 156 in the RFID-unit receptacle 216, illuminate the drainage receptacle 154, alert as to the status of the urine monitor 110 separately from or together with the GUI, alert as to the status of the patient separately from or together with the GUI, or a combination thereof. For example, the urine monitor 110 of FIGS. 2-4 includes a strip of LEDs 222 configured to directly illuminate the drainage receptacle 154 from a bottom thereof. The urine monitor 110 of FIGS. 2 and 3 also includes a strip of LEDs 224 behind a strip of diffusive material in the housing 212 configured to glow to indicate the state of the urine monitor 110 such as the "on" state of the urine monitor 110 or the active monitoring state of the urine monitor 110. Because the urine monitor of FIG. 4 includes the door 416, which would cover the strip of LEDs 224 if present, the urine monitor 110 of FIG. 4 includes sets of LEDs 426 behind pieces of the diffusive material in the housing 212 configured to glow to indicate the state of the urine monitor 110. For different states of the urine monitor 110, the LEDs 224 or 426 can be configured to illuminate in different colors, thereby providing color-coded visual alerts.

The user interface of the urine monitor 110 can further include aural features produced by, for example, one or more speakers to aurally indicate a state of the urine monitor 110 (e.g., the "on" state of the urine monitor 110, the active monitoring state of the urine monitor 110, etc.), indicate positive placement of the urine-collection system 150 in the cavity 214 or the RFID unit 156 in the RFID-unit receptacle 216, alert as to the status of the urine monitor 110, alert as to the status of the patient, or a combination thereof. For any alert of the foregoing visual and aural alerts, the user interface of the urine monitor 110 can be configured to provide the visual alert independent of the aural alert, the aural alert independent of the visual alert, or the visual and aural alerts together, simultaneously.

Weight-Based Urine Measurements in Urine Monitors

Figure 5:
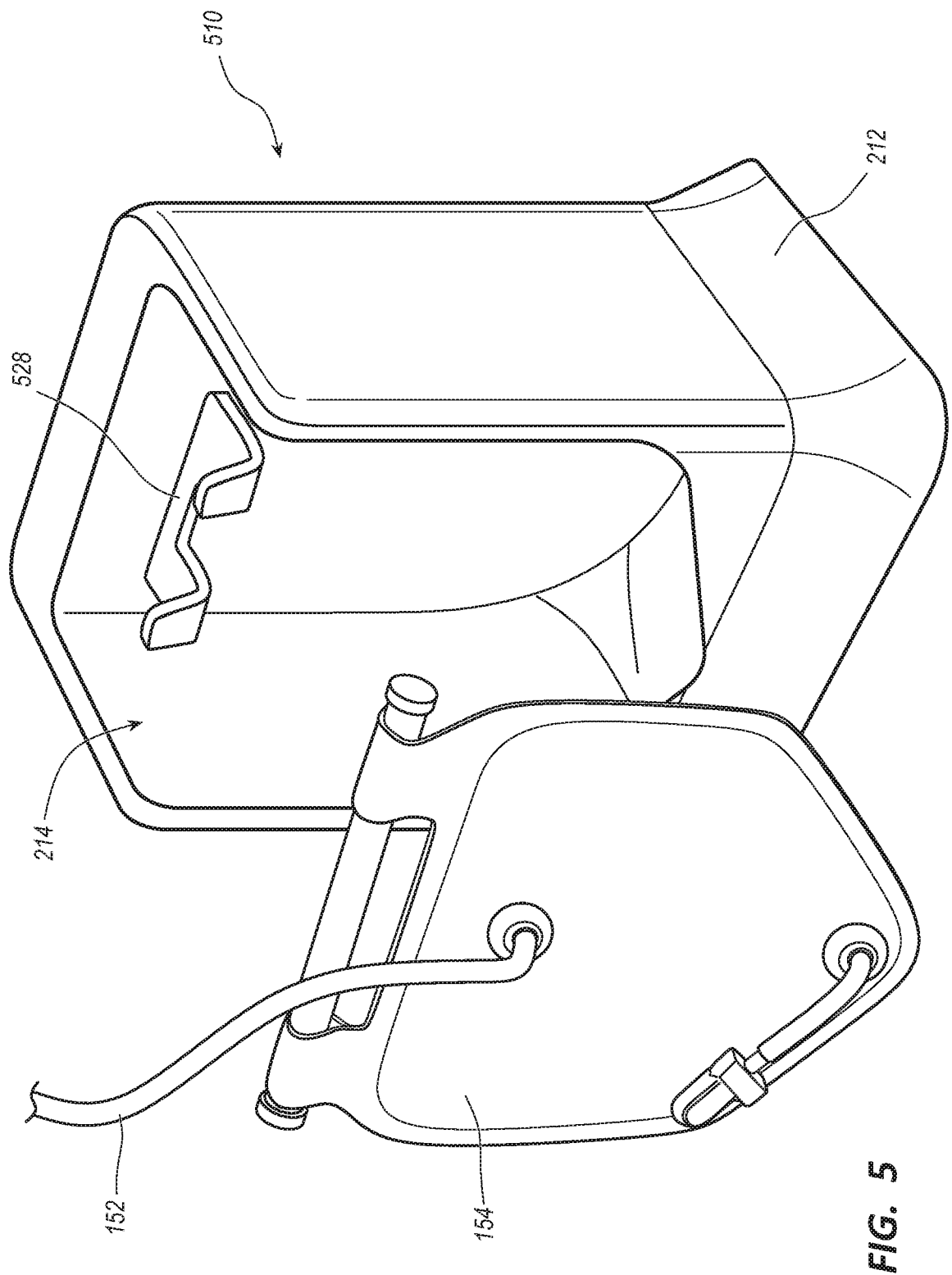
FIG. 5 illustrates a urine monitor of the automated urine-output-measurement system configured for weight-based urine measurements in accordance with some embodiments.
Figure 6:
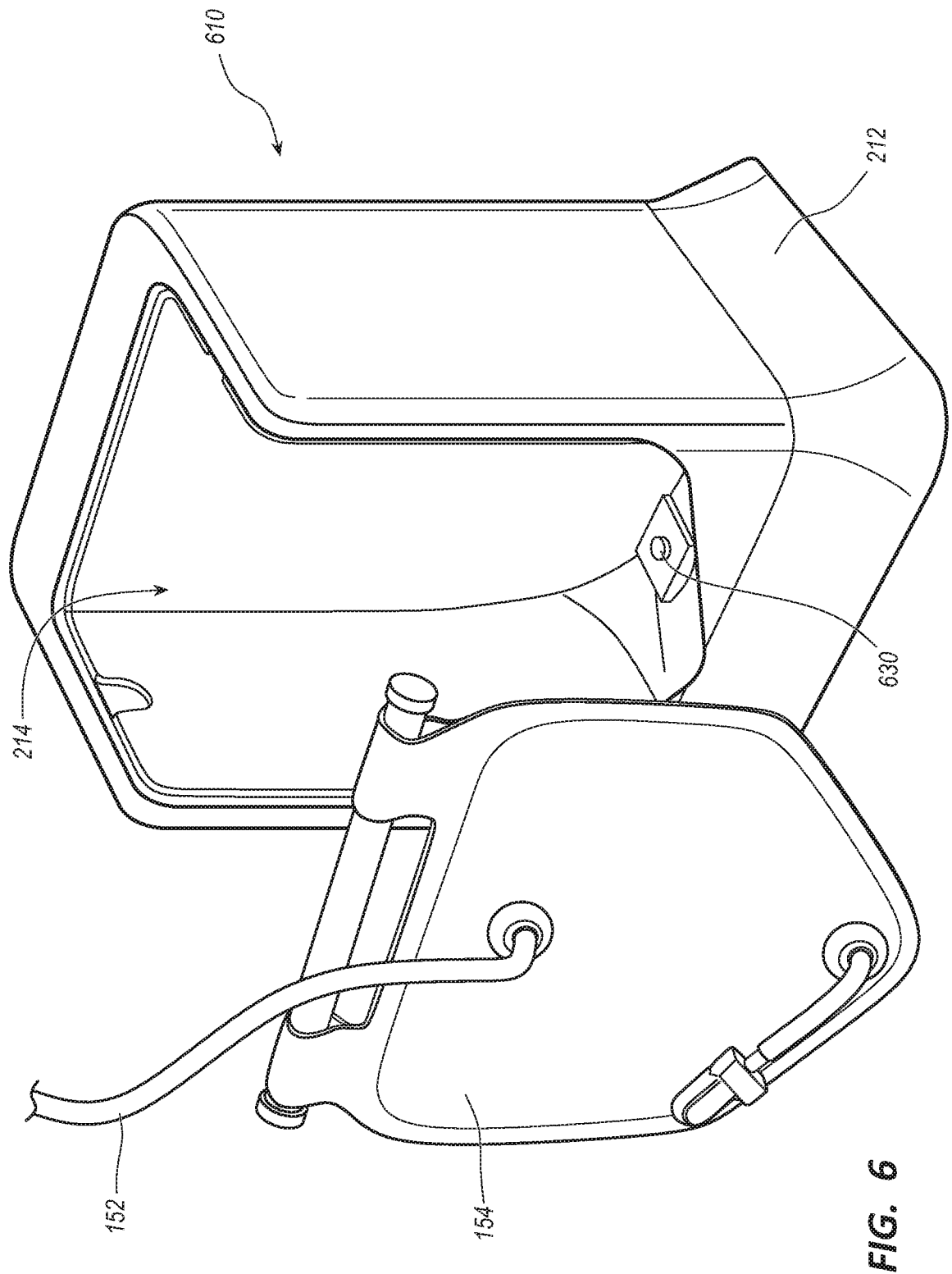
FIG. 6 illustrates a urine monitor of the automated urine-output-measurement system configured for weight-based urine measurements in accordance with some embodiments.

FIGS. 5 and 6 respectively illustrate urine monitors 510 and 610 of the automated urine-output-measurement system 100 configured for weight-based urine measurements in accordance with some embodiments. It should be understood the urine monitor 110 set forth herein such as in the description for FIGS. 2-4 set forth above is intended to be generic to the urine monitors 510 and 610. The urine monitors 510 and 610 inherit the features of the urine monitor 110 except those with respect to the urine-measurement means for measuring urine-output into the drainage receptacle 154, which are set forth below for the urine monitors 510 and 610.

While not directly shown in FIG. 5, the urine-measurement means of the urine monitor 510 for measuring urine output into the drainage receptacle 154 includes a load cell for weight-based urine-output measurements. The load cell is coupled to a load-bearing hook 528 located in a back of the cavity 214 such that a load of the drainage receptacle 154 is applied to the load cell while the drainage receptacle 154 hangs from the load-bearing hook 528. The load cell can be either a compression load cell or a tension load cell located within the housing 212 of the urine monitor 510 depending upon a mechanism by which the load-bearing hook 528 applies the load of the drainage receptacle 154 to the load cell.

The compression load cell can be mounted within the housing 212 under the keypad 220 (not shown) such that the compression load cell is positioned between the keypad 220 and a concealed portion of the load-bearing hook 528 extending into the housing 212. When the drainage receptacle 154 hangs from an exposed portion of the load-bearing hook 528 extending from the housing 212 into the cavity 214, the exposed portion of the load-bearing hook 528 moves toward a bottom of the urine monitor 510 while the concealed portion of the load-bearing hook 528 pivots into the load cell under the keypad 220, thereby directly applying the load of the drainage receptacle 154 to the compression load cell.

The tension load cell can be mounted within the housing 212 under both the keypad 220 and the concealed portion of the load-bearing hook 528 and coupled to the concealed portion of the load-bearing hook 528 by a coupling. When the drainage receptacle 154 hangs from the exposed portion of the load-bearing hook 528, the exposed portion of the load-bearing hook 528 moves toward the bottom of the urine monitor 510 while the concealed portion of the load-bearing hook 528 pivots toward the keypad 220, thereby indirectly applying the load of the drainage receptacle 154 to the tension load cell by pulling the load away from the tension load cell by the coupling.

As shown in FIG. 6, the urine-measurement means of the urine monitor 610 for measuring urine output into the drainage receptacle 154 includes a compression load cell 630 for weight-based urine-output measurements. The compression load cell 630 is located in a bottom of the cavity 214 of the urine monitor 610. When the drainage receptacle 154 sits on the bottom of the cavity 214, the drainage receptacle also sits on the compression load cell 630, thereby directly applying a load of the drainage receptacle 154 to the compression load cell 630.

As set forth below, software of the embedded system 1000 of the urine monitor 110 can be configured to collect a number of weight-based measurements over time from a compression load cell such as the compression load cell 630 or a tension load cell, which weight-based measurements can be stored in the embedded system 1000 for a number of days such as at least 29 days. At any time while monitoring urine output of a patient, the weight-based measurements can be wirelessly communicated to the companion wireless device 120 (e.g., a tablet computer) over, for example, Bluetooth® or Wi-Fi. As an intermediate device between the urine monitor 110 and one or more networked computers, the companion wireless device 120 can be configured by way of one or more software programs to update electronic medical records with patient information including the weight-based urine-output measurements or retrieve historical patient information from the electronic medical records. Furthermore, rates of urine output can be calculated by the urine monitor 110 from the weight-based measurements, which can also be wirelessly communicated to update the electronic medical record for the patient at any time.

Volume-Based Urine Measurements in Urine Monitors

Figure 7:
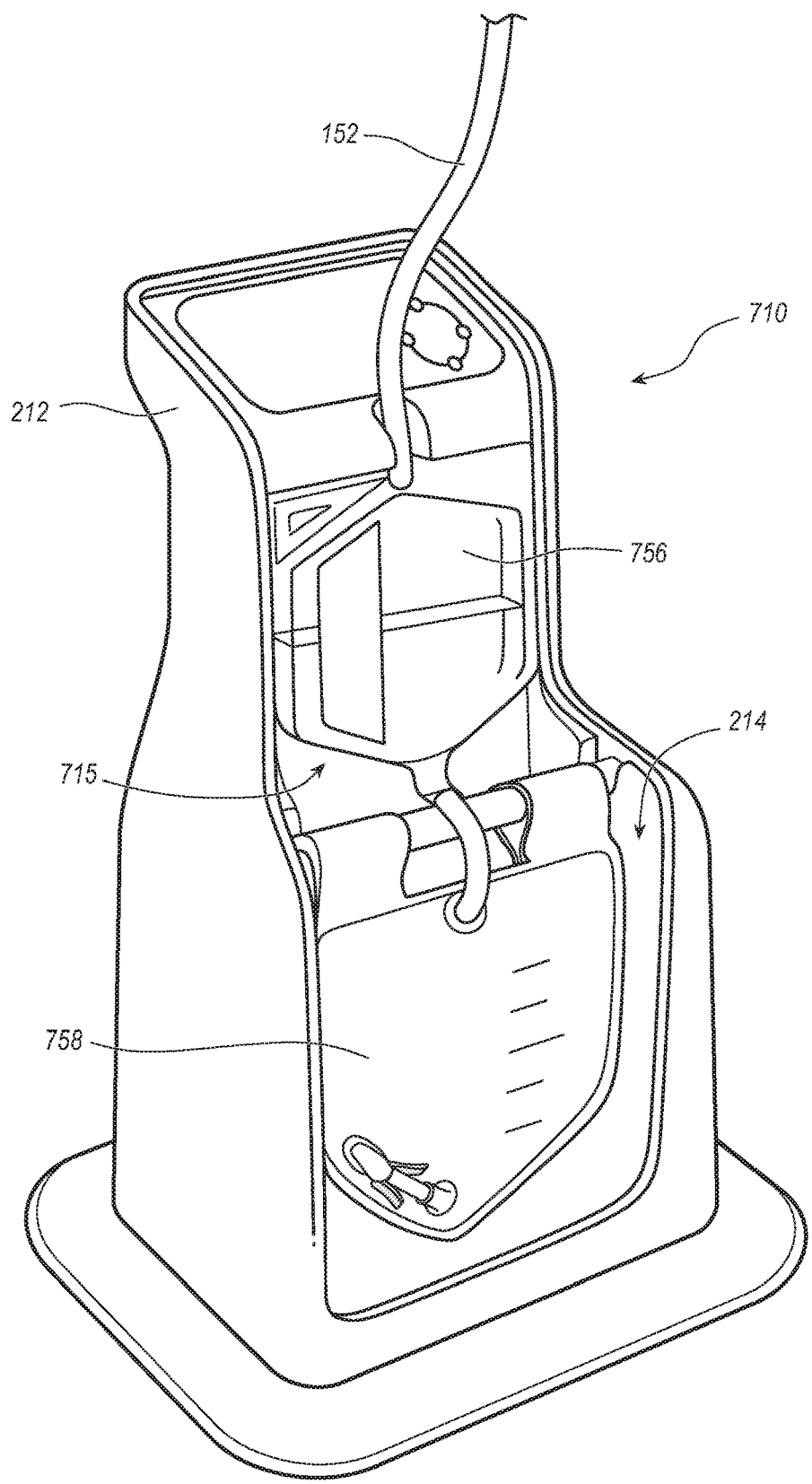
FIG. 7 illustrates a urine monitor of the automated urine-output-measurement system configured for volume-based urine measurements in accordance with some embodiments.

FIG. 7 illustrates a urine monitor 710 of the automated urine-output-measurement system 100 configured for volume-based urine measurements in accordance with some embodiments. It should be understood the urine monitor 110 set forth herein such as in the description for FIGS. 2-4 set forth above is intended to be generic to the urine monitor 710. The urine monitor 710 inherits the features of the urine monitor 110 except those with respect to the urine-measurement means for measuring urine-output into the drainage receptacle 154, which are set forth below for the urine monitor 710.

While not directly shown in FIG. 7, the urine-measurement means of the urine monitor 710 for measuring urine output into the drainage receptacle 154 employs a rigid- or hard-sided drainage cassette 756 for volume-based urine-output measurements. The drainage cassette 756 is configured to be fluidly coupled to a soft-sided drainage bag 758, thereby forming the drainage receptacle 154. In addition to the cavity 214 of the urine monitor 110, which is configured to house a drainage bag such as the drainage bag 758, the urine monitor 710 includes an upper extension 715 of the cavity 214 configured to house the drainage cassette 756.

The urine-measurement means of the urine monitor 710 for measuring urine output into the drainage receptacle 154 includes a contactless ultrasonic liquid-level sensor, a contactless optical liquid-level sensor, or an in-line flow meter for volume-based urine-output measurements. For the ultrasonic liquid-level sensor, the drainage cassette 756 can include a port in a top of the drainage cassette 756 for insertion of the ultrasonic liquid-level sensor adjacent a port in the top of the drainage cassette 756 for the drainage tubing 152. The ultrasonic liquid-level sensor can be tethered to the urine monitor 710 or provided with the single-patient equipment and subsequently connected to the urine monitor 710. For the optical liquid-level sensor, the optical liquid-level sensor or a number of such sensors can be recessed into the upper extension 715 of the cavity 214 behind the drainage cassette 756 or to a side of the drainage cassette 756. For the in-line flow meter, the in-line flow meter can be integrated into the drainage tubing port of the drainage cassette 756. Because urine flows through the in-line flow meter, the in-line flow meter can be provided with the single-patient equipment and subsequently connected to the urine monitor 710.

As set forth below, software of the embedded system 1000 of the urine monitor 110 can be configured to collect a number of volume-based measurements over time from the contactless ultrasonic liquid-level sensor, the contactless optical liquid-level sensor, or the in-line flow meter, which volume-based measurements can be stored in the embedded system 1000 for a number of days such as at least 29 days. At any time while monitoring urine output of a patient, the volume-based measurements can be wirelessly communicated to the companion wireless device 120 (e.g., a tablet computer) over, for example, Bluetooth® or Wi-Fi. As an intermediate device between the urine monitor 110 and one or more networked computers, the companion wireless device 120 can be configured by way of one or more software programs to update electronic medical records with patient information including the volume-based urine-output measurements or retrieve historical patient information from the electronic medical records. Furthermore, rates of urine output can be calculated by the urine monitor 110 from the volume-based measurements, which can also be wirelessly communicated to update the electronic medical record for the patient at any time.

RFID Reader-Writers in Urine Monitors

FIGS. 2-4, 8, 9A, and 9B illustrate urine monitors 110, 810, and 910 of the automated urine-output-measurement system 100 including RFID reader-writers, drainage-tubing strain-relief features, or a combination thereof in accordance with some embodiments. It should be understood the urine monitor 110 set forth herein such as in the description for FIGS. 2-4 set forth above is intended to be generic to the urine monitors 810 and 910. The urine monitors 810 and 910 inherit the features of the urine monitor 110 except those with respect to the RFID reader-writers and drainage-tubing strain-relief features, which are set forth below for each urine monitor of the urine monitors 110, 810, and 910.

As shown in FIGS. 2-4, the housing 212 of the urine monitor 110 can include the RFID-unit receptacle 216 configured to retain the RFID unit 156 (e.g., an RFID bead) when the RFID unit 156 is around a length of the drainage tubing 152 adjacent the drainage receptacle 154. In addition, the housing 212 includes a transverse drainage-tubing channel 217 including the RFID-unit receptacle 216 configured to accommodate the drainage tubing 152 on both sides of the RFID unit 156 when the RFID unit 156 is around the length of the drainage tubing 152 adjacent the drainage receptacle 154, as well as provide strain relief to the drain tubing 156 by guiding and supporting the drainage tubing 152 to prevent kinks therein. Because the RFID-unit receptacle 216 is configured to retain the RFID unit 156 when the RFID unit 156 is around the drainage tubing 152, the RFID-unit receptacle 216 is also configured to retain the drainage tubing 152 in the transverse drainage-tubing channel 217 by way of the RFID unit 156.

The urine monitor 110 can further include an RFID-unit reader-writer (not shown) within the housing 212 about the RFID-unit receptacle 216. The RFID-unit reader-writer is configured to identify a presence of the RFID unit 156, read patient information including measurements of urine output from the RFID unit 156, and write the patient information including the measurements of the urine output to the RFID unit 156.

Figure 8:
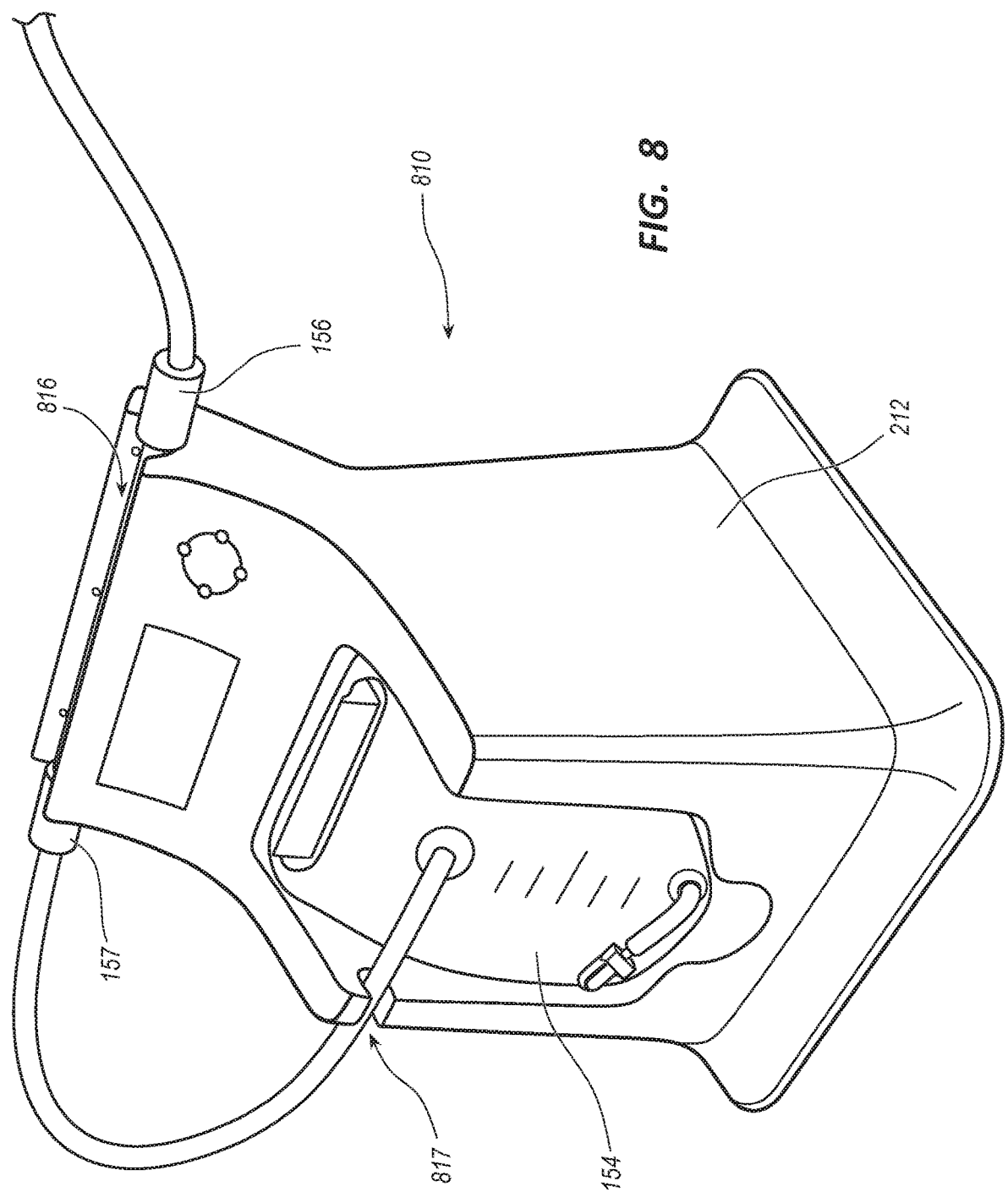
FIG. 8 illustrates a urine monitor of the automated urine-output-measurement system including an RFID reader-writer in accordance with some embodiments.

As shown in FIG. 8, the housing 212 of the urine monitor 810 can include a longitudinal drainage-tubing channel 816 and a companion drainage-tubing slot 817 configured to accommodate the drainage tubing 152, as well as provide strain relief to the drainage tubing 156 by guiding and supporting the drainage tubing 152 to prevent kinks therein. Different than the RFID-unit receptacle 216 of the urine monitor 110, the longitudinal drainage-tubing channel 816 is not configured to retain the RFID unit 156 like the RFID-unit receptacle 216. Instead, the RFID unit 156 and either a backup or faux RFID unit 157 around opposing portions of a length of the drainage tubing 152 are configured to retain the drainage tubing 152 in the longitudinal drainage-tubing channel 816 by a slight compressive force between the RFID units 156 and 157. The slight compressive force between the RFID units 156 and 157 results from applying a slight tensile force on the drainage tubing 152 between the RFID units 156 and 157 such as by pulling before disposing the drainage tubing 152 in the longitudinal drainage-tubing channel 816.

The urine monitor 810 can further include an RFID-unit reader-writer (not shown) within the housing 212 about the longitudinal drainage-tubing channel 816 such as on either minor side of the urine monitor 810 for the RFID units 156 and 157 when the RFID unit 157 is a faux RFID unit. Alternatively, the urine monitor 810 can further include two RFID-unit reader-writers (not shown) within the housing 212 about the longitudinal drainage-tubing channel 816 such as on both minor sides of the urine monitor 810 for the RFID units 156 and 157 when the RFID unit 157 is a backup RFID unit. Each RFID-unit reader-writer of the foregoing RFID-unit reader-writers is configured to identify a presence of the RFID unit 156 or 157, read patient information including measurements of urine output from the RFID unit 156 or 157, and write the patient information including the measurements of the urine output to the RFID unit 156 or 157.

Figure 9B:
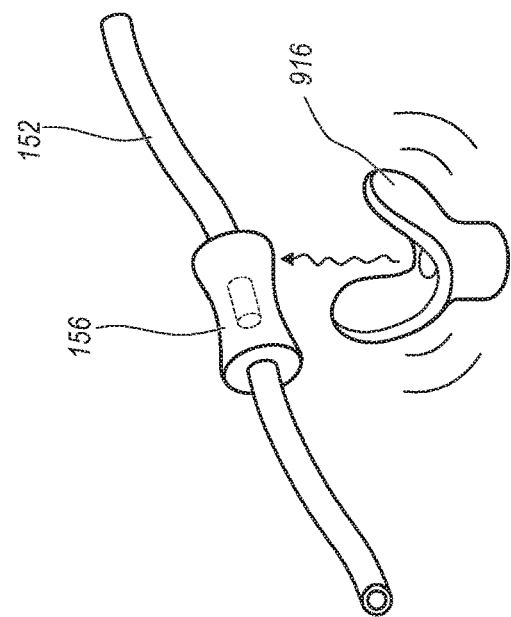
FIG. 9B illustrates a close-up view of the RFID reader-writer of FIG. 13A.
Figure 9A:
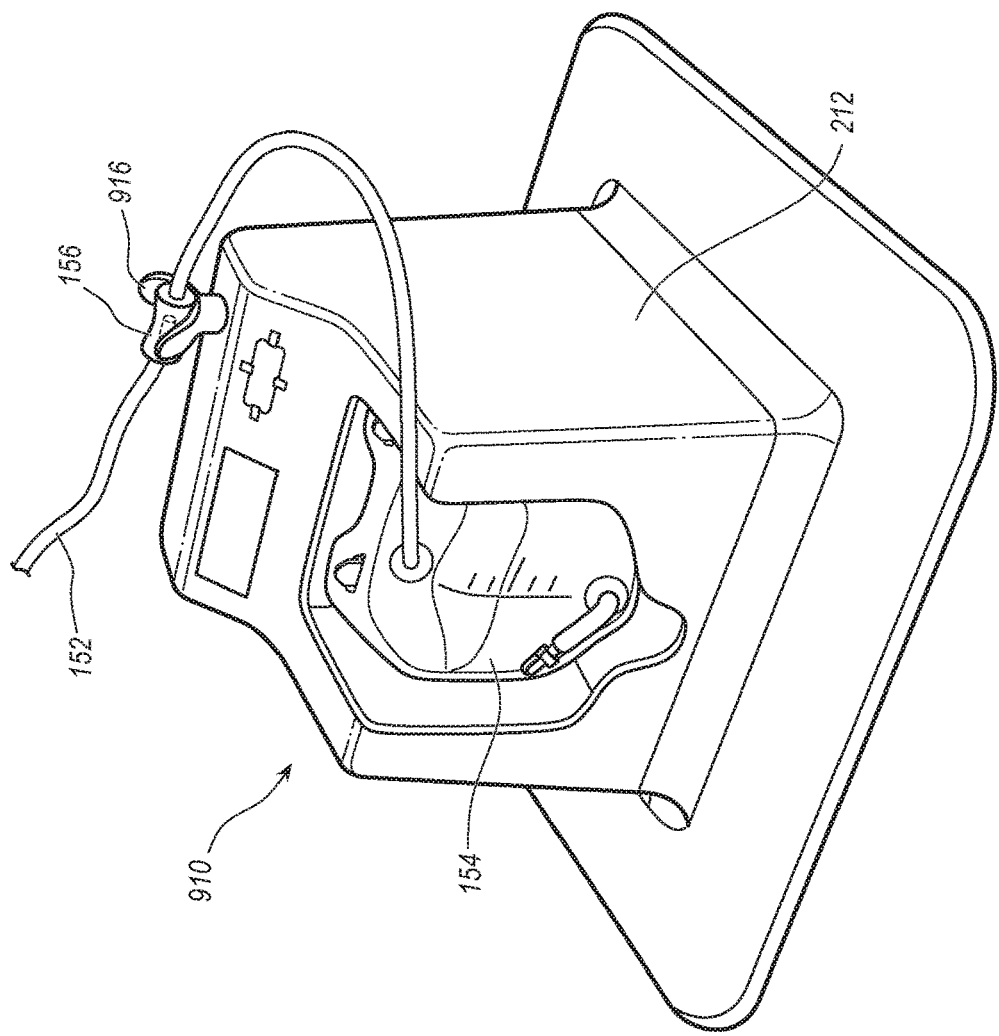
FIG. 9A illustrates a urine monitor of the automated urine-output-measurement system including an RFID reader-writer in accordance with some embodiments.

As shown in FIGS. 9A and 9B, the urine monitor 910 can include an RFID-unit holder 916 disposed in the housing 212 of the urine monitor 910 configured to retain the RFID unit 156 (e.g., an RFID bead) when the RFID unit 156 is around a length of the drainage tubing 152 adjacent the drainage receptacle 154. Because the RFID-unit holder 916 is configured to retain the RFID unit 156 when the RFID unit 156 is around the drainage tubing 152, the RFID-unit holder 916 is also configured to retain the drainage tubing 152, as well as provide strain relief to the drain tubing 156 by guiding and supporting the drainage tubing 152 to prevent kinks therein.

The urine monitor 910 can further include an RFID-unit reader-writer (not shown) within the RFID-unit holder 916. The RFID-unit reader-writer is configured to identify a presence of the RFID unit 156, read patient information including measurements of urine output from the RFID unit 156, and write the patient information including the measurements of the urine output to the RFID unit 156.

Embedded System

Figure 10:
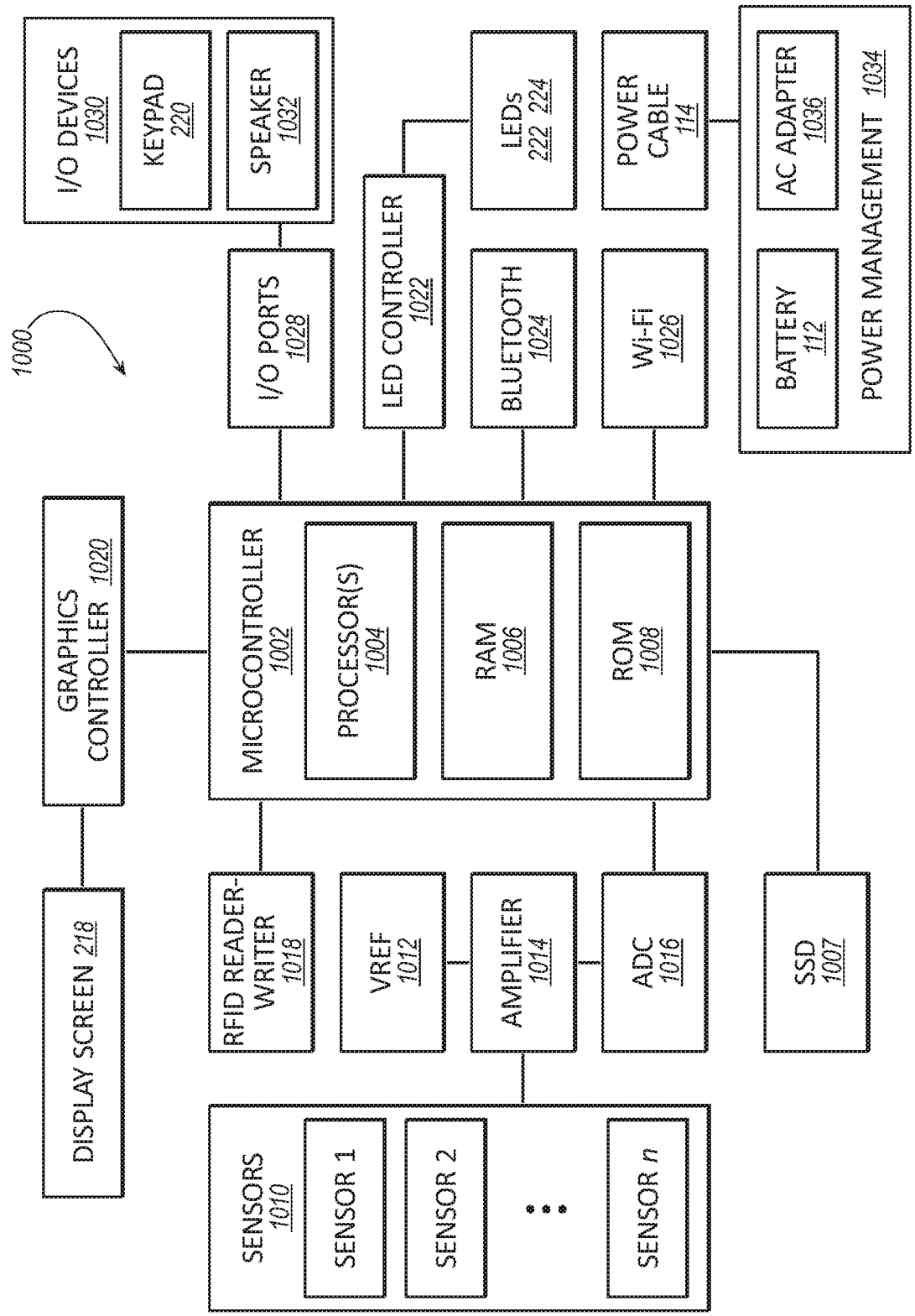
FIG. 10 illustrates an embedded system of the urine monitor in accordance with some embodiments.

FIG. 10 illustrates an embedded system 1000 of the urine monitor 110 in accordance with some embodiments.

As shown, the embedded system 1000 can include a microcontroller 1002 having one or more processors 1004 configured to process data from random-access memory ("RAM") 1006 or a solid-state storage device such as a solid-state drive ("SSD") 1007 in accordance with instructions in the RAM 1006 for processing the data of the microcontroller 1002. In addition to the RAM 106, the microcontroller 1002 can include read-only memory ("ROM") 1008 configured to store software such as firmware for operating the urine monitor 110.

As set forth above, the urine monitor 110 can be configured with a weight- or volume-based urine-measurement means for measuring urine output into the drainage receptacle 154, each of which urine-measurement means utilizes one or more sensors 1010 communicatively coupled to the embedded system 1000. For example, the one or more sensors 1010 can be selected from the compression load cell, the tension load cell, the contactless ultrasonic liquid-level sensor, the contactless optical liquid-level sensor, and the in-line flow meter set forth above. In addition to the one or more sensors 1010, the embedded system 1000 can further include a voltage reference ("VREF") configured to provide a stable reference voltage for signals from the one or more sensors 1010, an amplifier 1014 configured to amplify the signals from the one or more sensors 1010, and an analog-to-digital converter ("ADC") 1016 configured to convert the signals from the one or more sensors 1010 into the data for the one or more processors 1004 to process.

As set forth above, the urine monitor 110 can be configured to include an RFID reader-writer or a pair of RFID reader-writers, each of which RFID reader-writers is communicatively coupled to the embedded system 1000 as shown by RFID reader-writer 1018 of FIG. 10.

The embedded system 1000 can further include a dedicated or virtual graphics controller 1020 configured to control rendering of the GUI and patient information including urine-output measurements on the integrated display screen 218 of the urine monitor 110; an LED controller 1022 configured to control the strips of LEDs 222 and 224; one or more wireless communication modules selected from at least a Bluetooth® module 1024 and a Wi-Fi module 1026 configured for wirelessly communicating at least the patient information including the urine-output measurements with the companion wireless device 120 (e.g., a tablet computer) when paired; and I/O ports 1028 configured for communicatively coupling one or more I/O devices 1030 such as the keypad 220 or a speaker 1032 such as the speaker set forth above with respect to aural alerts.

Lastly, the embedded system 1000 can include power management 1034 including at least the one or more batteries 112, the power cable 114, and an AC adapter configured to convert AC electrical power from the general-purpose AC electrical power supply into direct current ("DC") for at least charging the one or more batteries 112.

Environments for the Automated Urine-Output-Measurement System

Figure 11:
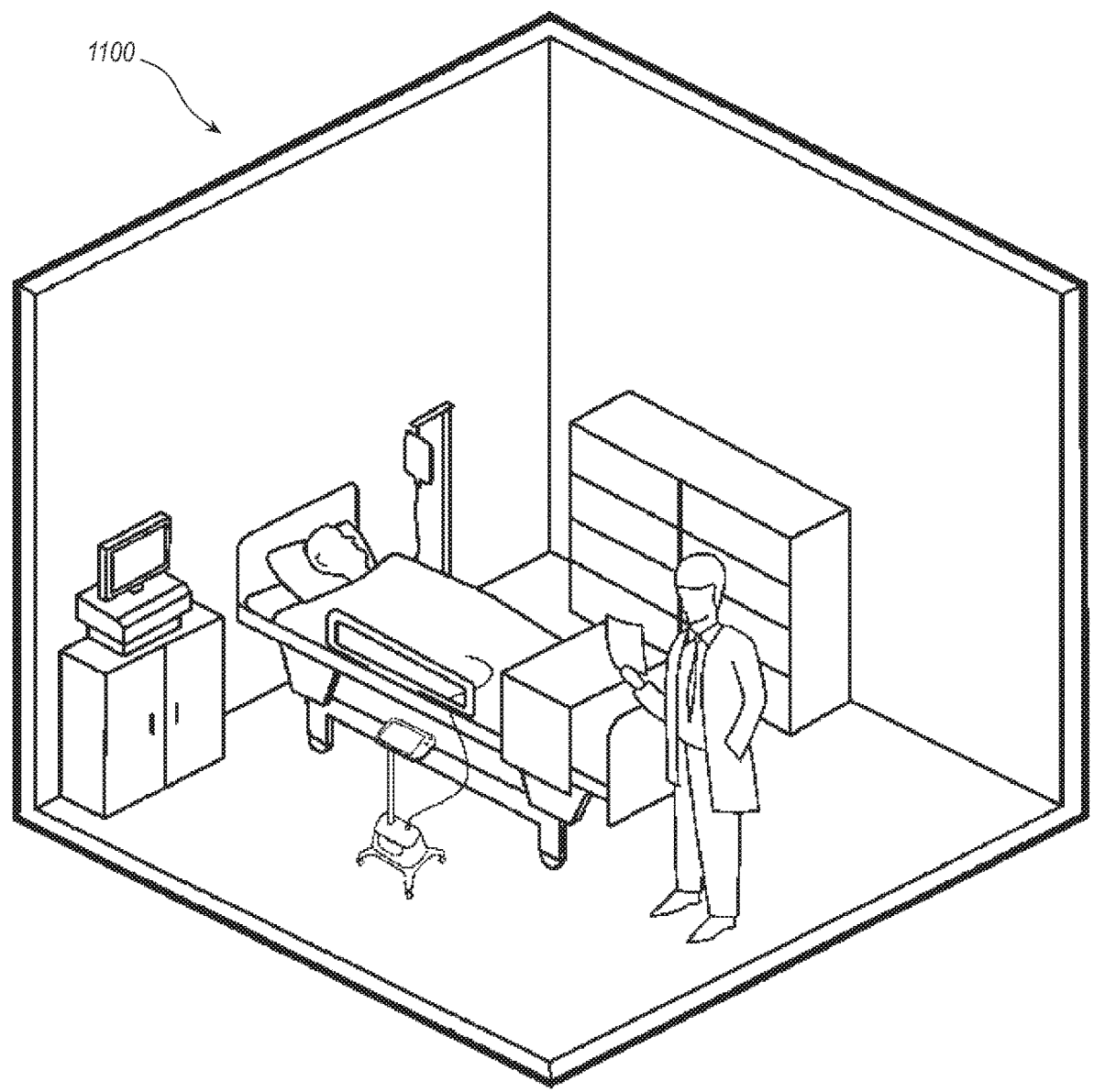
FIG. 11 illustrates a first scenario in which the automated urine-output-measurement system is effective.
Figure 12:
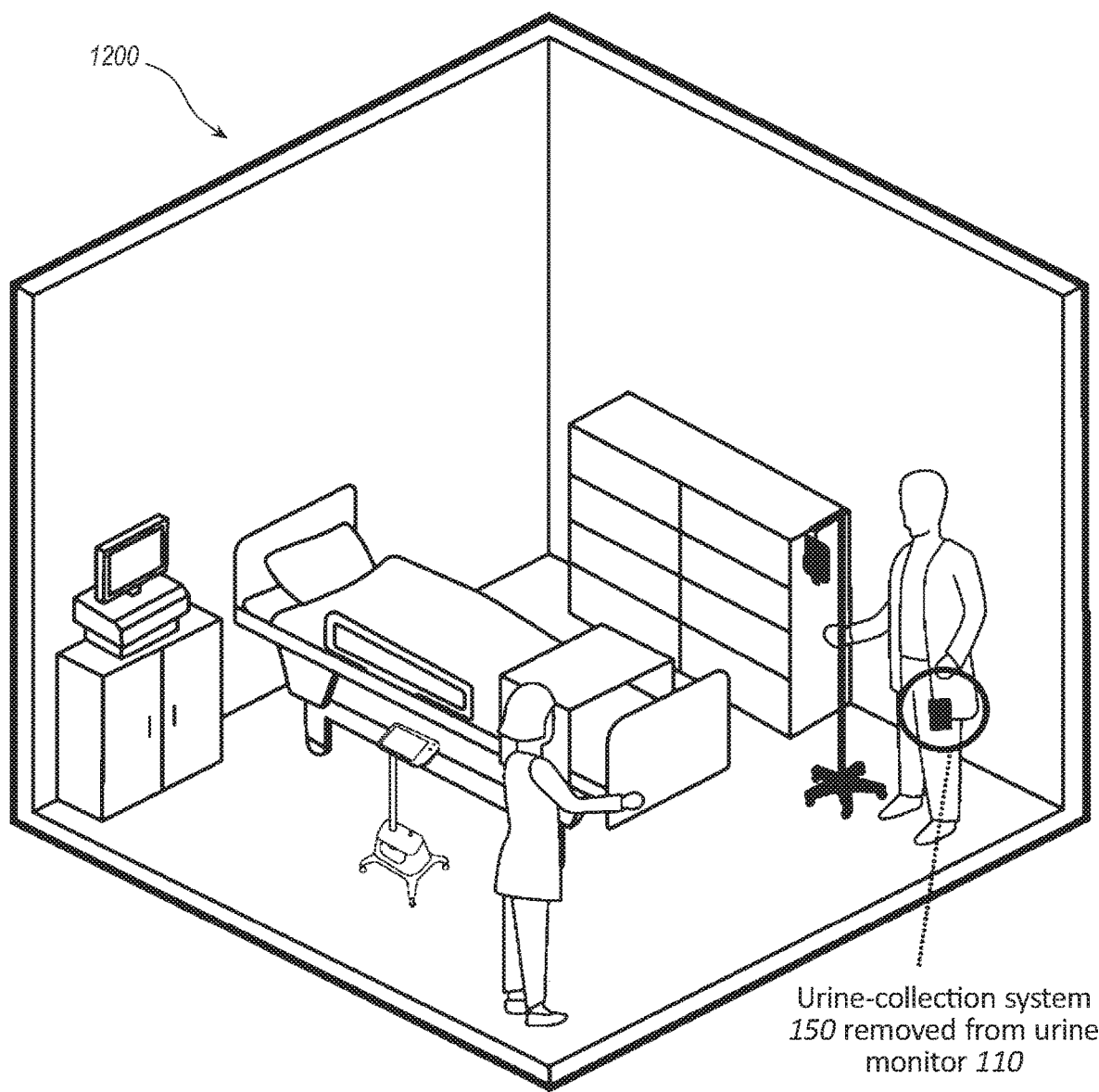
FIG. 12 illustrates a second scenario in which the automated urine-output-measurement system is effective.

FIG. 11 illustrates a first scenario in which the automated urine-output-measurement system 100 is effective. FIG. 12 illustrates a second scenario in which the automated urine-output-measurement system is effective.

As shown, the first scenario of FIG. 11 includes a bed-ridden patient in a hospital room. Since the patient cannot leave his or her hospital bed, it is notable that the automated urine-output-measurement system 100 can be configured to not crowd the space around the hospital bed whether mounted on an IV pole or a bed rail respectively by way of the IV-pole mount 132 or the bed-rail mount 134.

As shown, the second scenario of FIG. 12 includes an able-bodied patient in a hospital room. Since the patient can leave his or her hospital bed, it is notable that the automated urine-output-measurement system 100 can be configured to travel with the patient when mounted on the floor stand 136. Indeed, the urine monitor 110 can be configured to facilitate transport through a number of different environments other than the foregoing hospital room while in operation. The urine monitor 110 can even be configured with a transport mode that limits collection of certain data (e.g., urine-output measurements) and any alarms, as applicable.

Urine-Clearing Device

Figure 13:
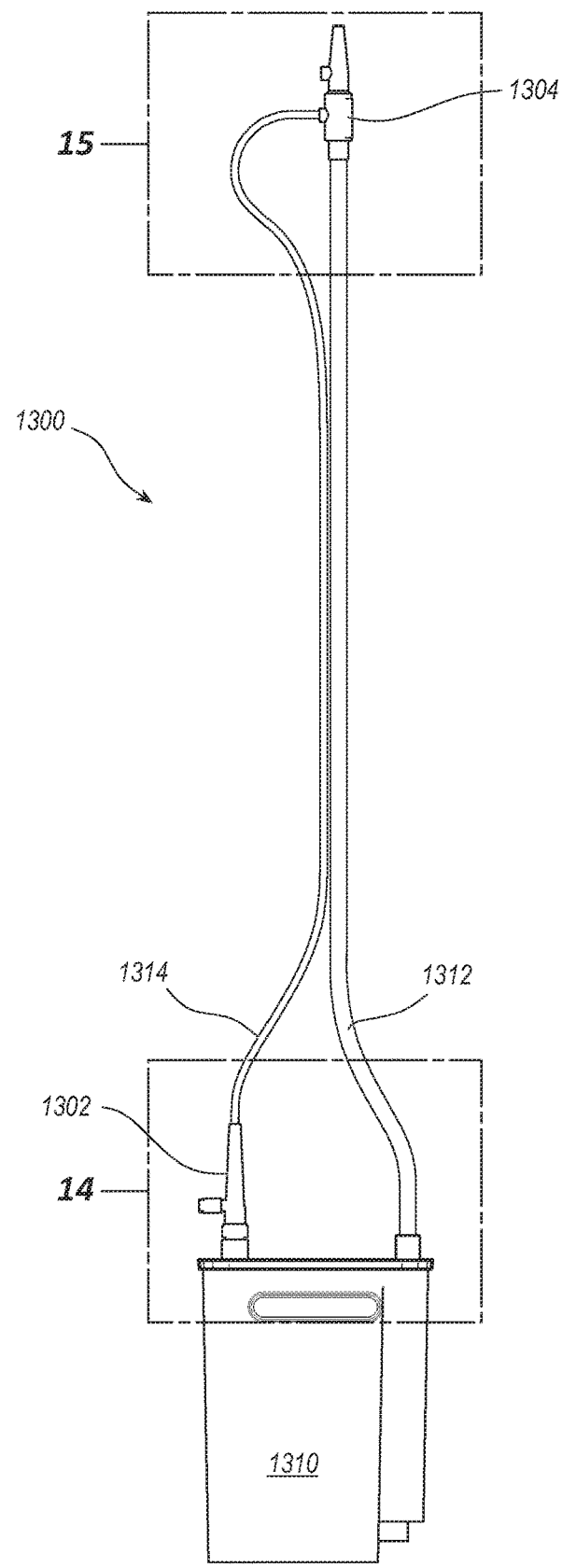
FIG. 13 illustrates a urine-clearing device for clearing urine from drainage tubing in accordance with some embodiments.
Figure 14:
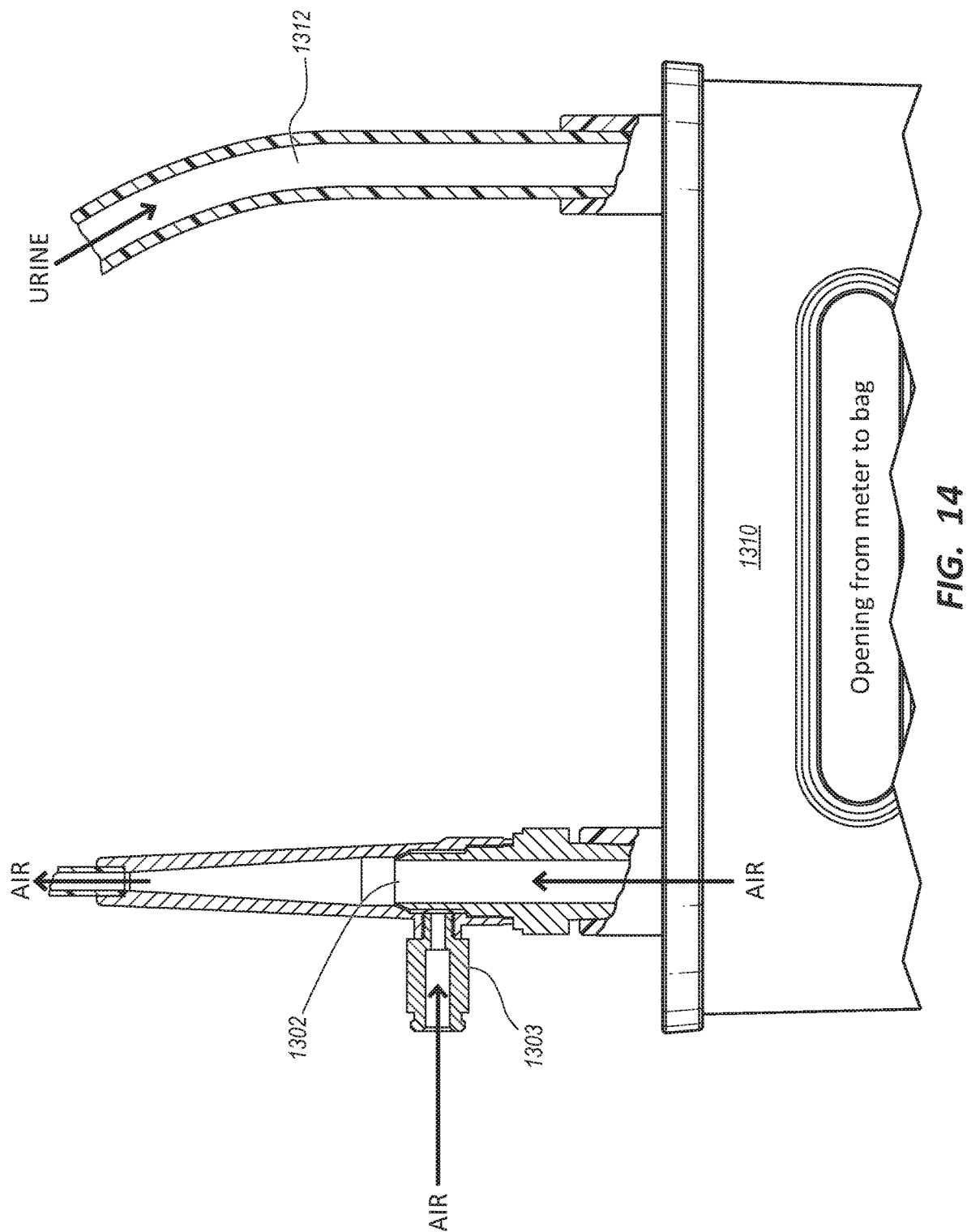
FIG. 14 illustrates a suction educator of the urine-clearing device of FIG. 13.
Figure 15:
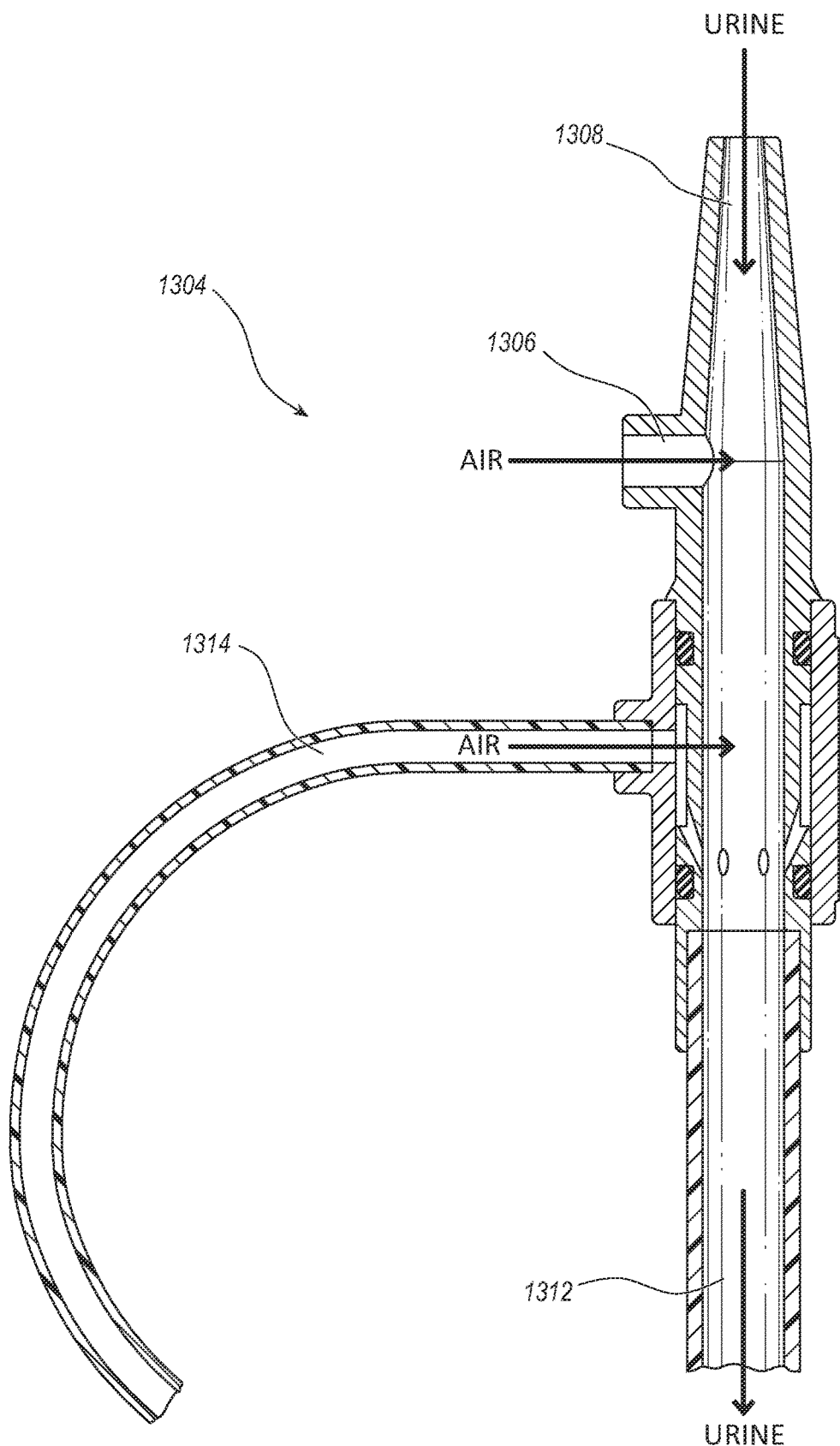
FIG. 15 illustrates a ring nozzle of the urine-clearing device of FIG. 13.

FIG. 13 illustrates a urine-clearing device 1300 for clearing urine from the drainage tubing 152 in accordance with some embodiments. FIG. 14 illustrates a suction eductor 1302 of the urine-clearing device 1300 of FIG. 13. FIG. 15 illustrates a ring nozzle 1304 of the urine-clearing device 1300 of FIG. 13.

As shown, the urine-clearing device 1300 can include the suction eductor 1302 having a port 1303, the ring nozzle 1304 having a vent 1306 and a port connector 1308, a urine meter 1310, and both drainage tubing 1312 and ring-nozzle supply tubing 1314 therebetween. The urine-clearing device 1300 can be considered part of the urine-collection system 150, wherein the urine-clearing device 1300 is configured to clear residual urine from the urinary catheter 140 or the drainage tubing 152 by way of connecting the port connector 1308 to a drainage port of a tubing connector fluidly connecting the urinary catheter 140 and the drainage tubing 152. As illustrated in FIGS. 14 and 15 by the fluid-flow arrows, air introduced to the urine-clearing device 1300 through the port 1303 of the suction eductor 1302 pulls air from the urine meter 1310 through the ring-nozzle supply tubing 1314 to the ring nozzle 1304, which creates a vacuum for clearing the residual urine from the urinary catheter 140 or the drainage tubing 152 through the drainage port of the tubing connector. The vent 1306 of the ring nozzle 1304 is configured to provide control over the vacuum for clearing the residual urine from the urinary catheter 140 or the drainage tubing 152.

Methods

FIGS. 16-27 respectively provide methods 1600-2700 of the automated urine-output-measurement system 100. While the methods 1600-2700 are presented separately around certain aspects of using the automated urine-output-measurement system 100, it should be understood that the methods 1600-2700 are presented separately as a matter of expository expediency. Any method of the methods 1600-2700 can be combined with any other method or methods of the methods 1600-2700 for using the automated urine-output-measurement system 100.

Figure 16:
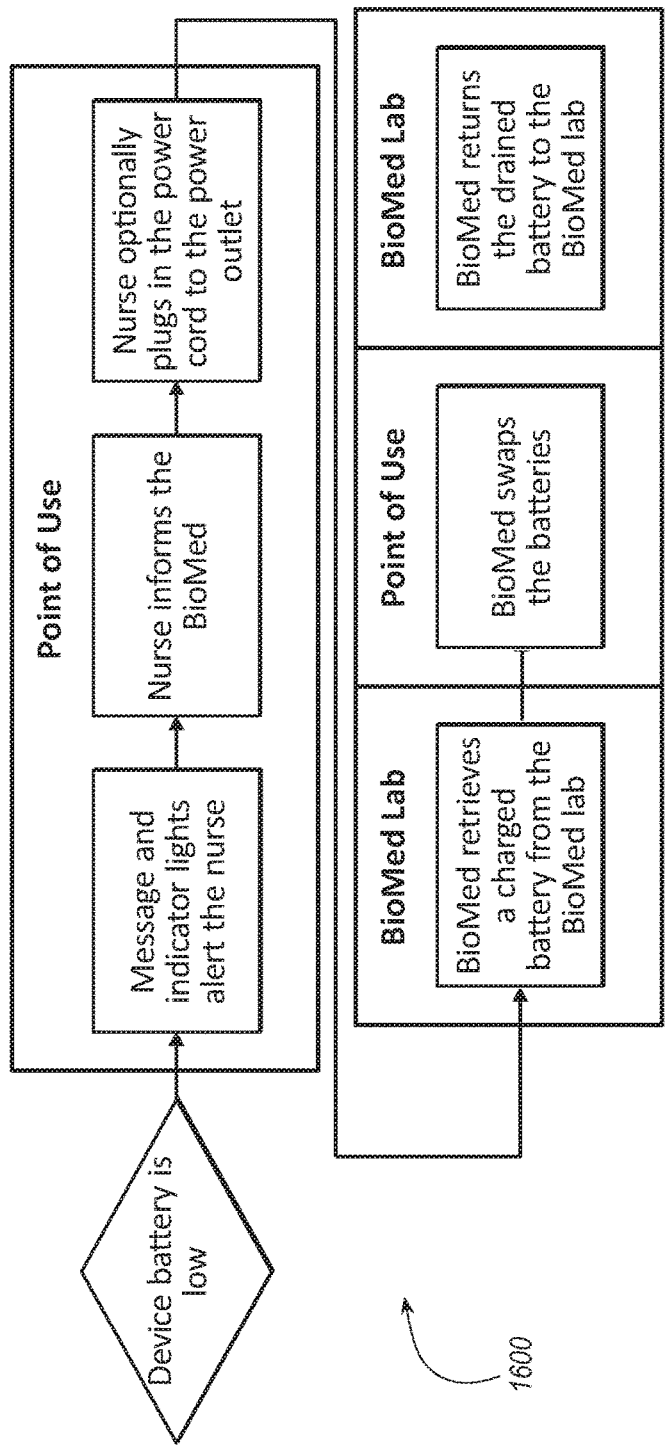
FIG. 16 illustrates a method for replacing a battery in a urine monitor of an automated urine-output-measurement system when the battery is low in accordance with some embodiments.

FIG. 16 illustrates a method 1600 for replacing a battery of the one or more rechargeable batteries 112 in the urine monitor 110 of the automated urine-output-measurement system 100 when the battery is low in accordance with some embodiments.

As shown, the method 1600 includes a number of steps at a point of use of the automated urine-output-measurement system 100 and a biomedical lab, a central supply room ("CSR"), or the like.

The method 1600 includes a step of displaying a message on the integrated display screen 218 of the urine monitor 110 and providing a visual alert to alert a clinician such as a nurse the battery is a low-charge battery. The method 1600 further includes a step of the clinician informing the biomedical lab of the low-charge battery. The method 1600 optionally includes a step of the clinician plugging in the power cable 114 into a receptacle of a general-purpose alternating-current electrical power supply. The method 1600 further includes a step of a person such as an employee of the biomedical lab retrieving for the clinician a charged battery. The method 1600 further includes a step of the employee swapping the low-charge battery out with the charged battery. The method 1600 further includes a step of the employee returning the low-charge battery to the biomedical lab. While not shown, the method 1600 can further include a step of the employee charging the low-charge battery with the external battery-charging device.

Figure 17:
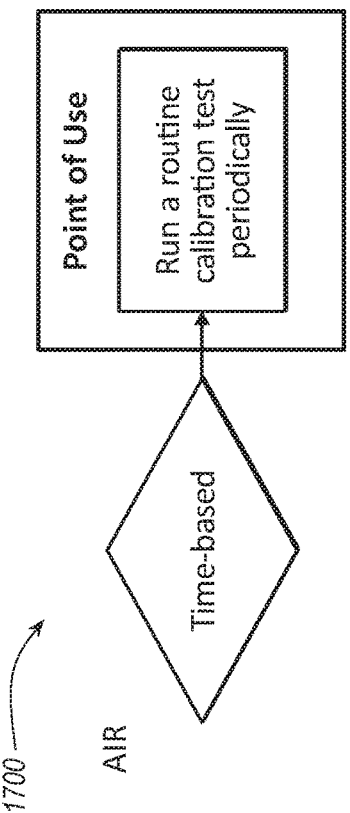
FIG. 17 illustrates a method for performing a routine calibration test for a urine monitor of an automated urine-output-measurement system in accordance with some embodiments.

FIG. 17 illustrates a method 1700 for performing a routine calibration test for the urine monitor 110 of the automated urine-output-measurement system 100 in accordance with some embodiments.

As shown, the method 1700 includes periodically running the routine calibration test for the urine monitor 110 at the point of use of the automated urine-output-measurement system 100.

FIG. 18 illustrates a method 1800 for servicing the urine monitor 110 of the automated urine-output-measurement system 100 when the urine monitor 110 needs service in accordance with some embodiments.

As shown, the method 1800 includes a number of steps at a point of use of the automated urine-output-measurement system 100 and a biomedical lab, a CSR, or the like.

The method 1800 includes a step of a person such as an employee of the biomedical lab retrieving the urine monitor 110 from the point of use. The method 1800 further includes a step of the employee replacing one or more user-serviceable modules of the urine monitor 110. If the user-serviceable module replacements are successful, the method 1800 further includes a step of the employee returning the urine monitor 110 to the point of use. If the user-serviceable module replacements are unsuccessful, the method 1800 further includes a step of the employee or another person like the employee of the biomedical lab sending the urine monitor 110 out to a manufacturer or another repair-service provider for service. If the service is successful or a replacement urine monitor 110 is provided, the method 1800 further includes a step of the employee delivering the urine monitor 110 to the point of use.

FIG. 19 illustrates a method 1900 for hot-swapping a battery of the one or more rechargeable batteries 112 in the urine monitor 110 of the automated urine-output-measurement system 100 when the battery is low in accordance with some embodiments.

As shown, the method 1900 includes a step of maintaining an inventory of charged batteries in a biomedical lab, a CSR, or the like for hot-swapping the battery of the one or more rechargeable batteries 112 in the urine monitor 110.

FIG. 20 illustrates a method 2000 for updating software in the urine monitor 110 of the automated urine-output-measurement system 100 when a software update is available in accordance with some embodiments.

As shown, the method 2000 includes a step of a clinician such as a nurse or a person such as an employee of a biomedical lab, a CSR, or the like looking at a splash screen of the GUI of the integrated display screen 218 of the urine monitor 110 to check a software version number for the software update. The method 2000 further includes a step of the nurse or the employee performing the software update on the urine monitor 110 at a point of use of the automated urine-output-measurement system 100.

Figure 21:
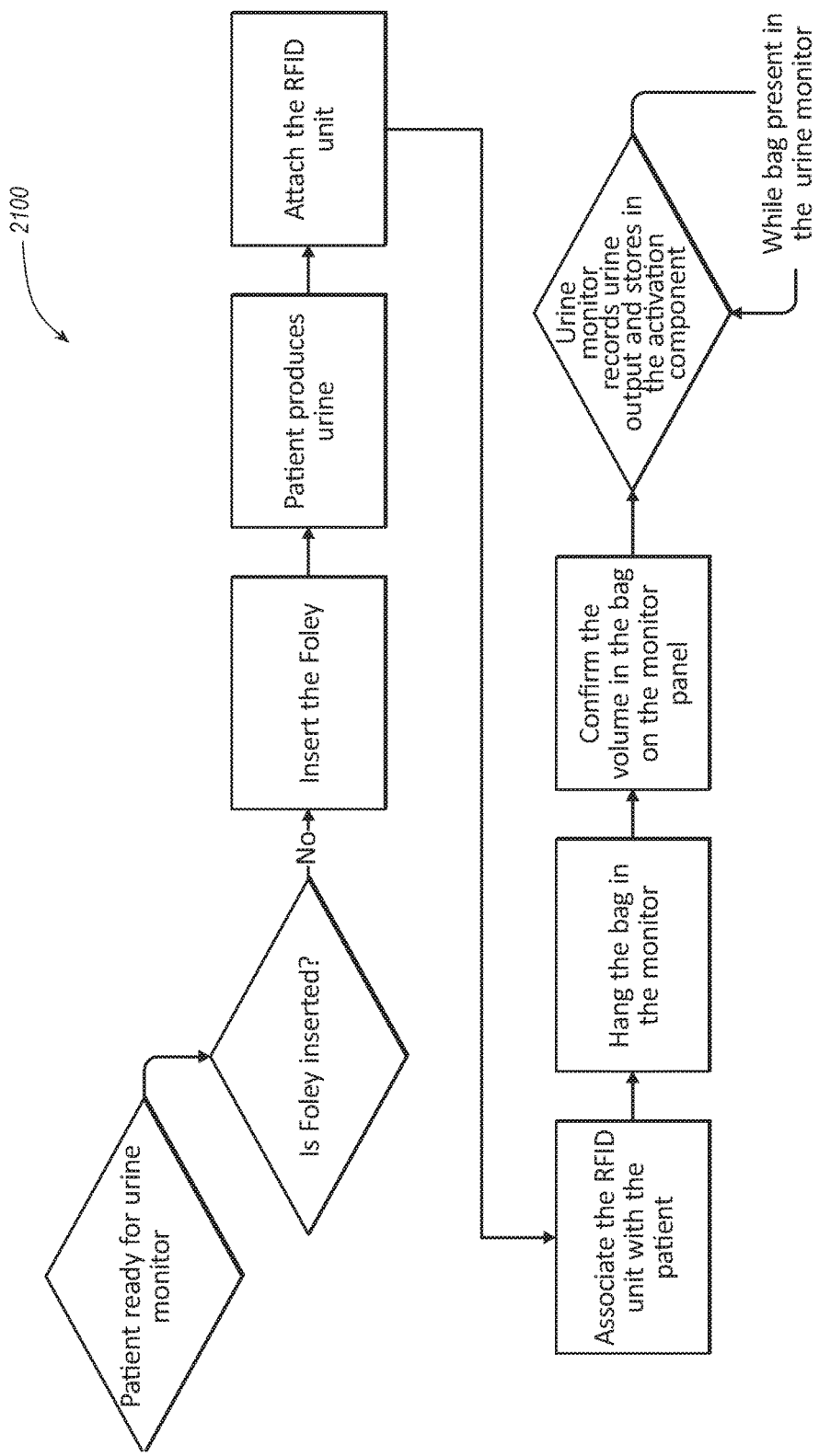
FIG. 21 illustrates a method for monitoring a urine output of a patient using an automated urine-output-measurement system in accordance with some embodiments.

FIG. 21 illustrates a method 2100 for monitoring urine output of a patient using the automated urine-output-measurement system 100 in accordance with some embodiments.

As shown, the method 2100 includes a step of a clinician such as a nurse inserting the urinary catheter 140, for example, a Foley catheter into the patient if the Foley catheter is not already inserted into the patient. The method 2100 further includes a step of the clinician confirming the Foley catheter is properly inserted upon observing the patient producing urine from the Foley catheter. The method 2100 further includes a step of the clinician attaching an activation component such as the RFID unit 156 to, for example, the drainage tubing 152 of the urine-collection system 150 if the activation component is not already attached to the drainage tubing 152. The method 2100 further includes a step of the clinician associating the activation component with the patient by way of, for example, the GUI of the integrated display screen 218 of the urine monitor 110. The method 2100 further includes a step of the clinician disposing or placing the drainage receptacle 154 such as a drainage bag in the cavity 214 of the housing 212 of the urine monitor 110 such as by hanging the drainage bag therein. The method 2100 further includes a step of the clinician confirming a volume of the urine in the drainage bag with that indicated on the integrated display screen 218 of the urine monitor 110 once the patient has produced urine. While the drainage bag is present in the urine monitor 110, the urine monitor 110 is configured to continuously record the volume of the urine in the drainage bag and record the volume of the urine in the drainage bag on the activation component.

Figure 22:
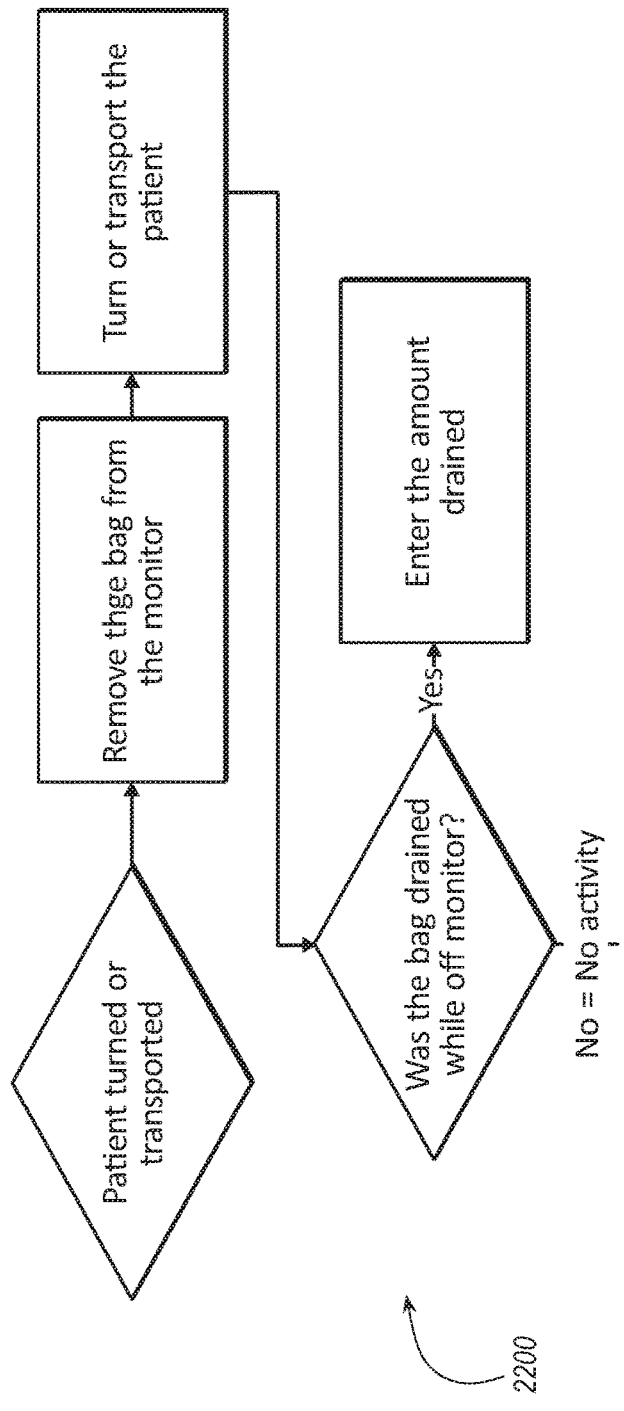
FIG. 22 illustrates a method for moving a patient when the patient is being monitored for urine output using an automated urine-output-measurement system in accordance with some embodiments.

FIG. 22 illustrates a method 2200 for moving a patient when the patient is being monitored for urine output using the automated urine-output-measurement system 100 in accordance with some embodiments.

As shown, the method 2200 includes a step of a clinician such as a nurse removing the drainage receptacle 154, for example, a drainage bag from the cavity 214 of the housing 212 of the urine monitor 110. The method 2200 includes a step of at least the clinician turning the patient in a hospital bed or transporting the patient to another hospital bed. The method 2200 optionally includes a step of the clinician draining urine form the drainage bag while the urine-collection system 150 is apart from the urine monitor 110. If the clinician drained the drainage bag in accordance with the foregoing step, the method 2200 includes a step of the clinician entering into the GUI of the integrated display screen 218 of the urine monitor 110 an amount of the urine drained from the drainage bag while the urine-collection system 150 was apart from the urine monitor 110. If the clinician did not drain the drainage bag while the urine-collection system 150 was apart from the urine monitor 110, the method 2200 can include a step of the clinician entering into the GUI of the integrated display screen 218 of the urine monitor 110 no amount of the urine was drained from the drainage bag while the urine-collection system 150 was apart from the urine monitor 110.

Figure 23:
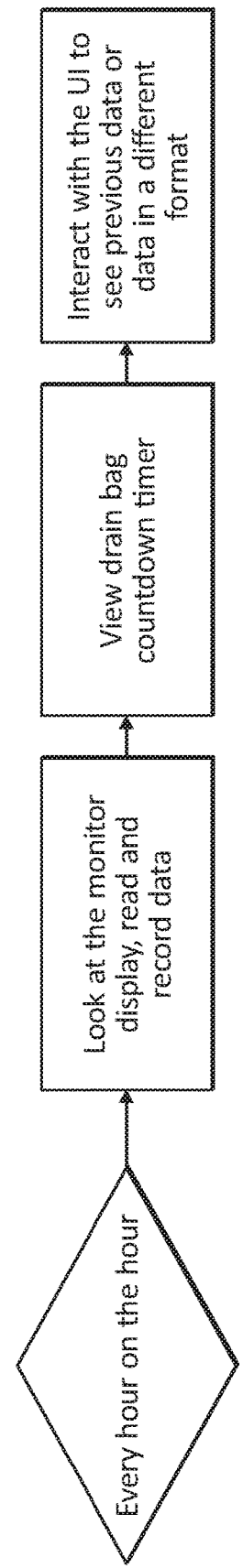
FIG. 23 illustrates a method for monitoring urine output of a patient using an automated urine-output-measurement system in accordance with some embodiments.

FIG. 23 illustrates a method 2300 for monitoring urine output of a patient using the automated urine-output-measurement system 100 in accordance with some embodiments.

As shown, the method 2300 includes a step of a clinician such as a nurse monitoring the urine output of the patient by viewing the integrated display screen 218 of the urine monitor 110 every hour, reading patient information including measurements of the urine output, and recording at least the measurements of the urine output. If a countdown timer is implemented on the integrated display screen 218 of the urine monitor 110, the method 2300 optionally includes a step of the clinician checking the drainage receptacle 154 such as a drainage bag for at least draining urine form the drainage bag if needed. The method 2300 further includes a step of the clinician interacting with the GUI of the integrated display screen 218 of the urine monitor 110 to view historical patient information including the measurements of the urine output or the patient information in a different format.

Figure 24:
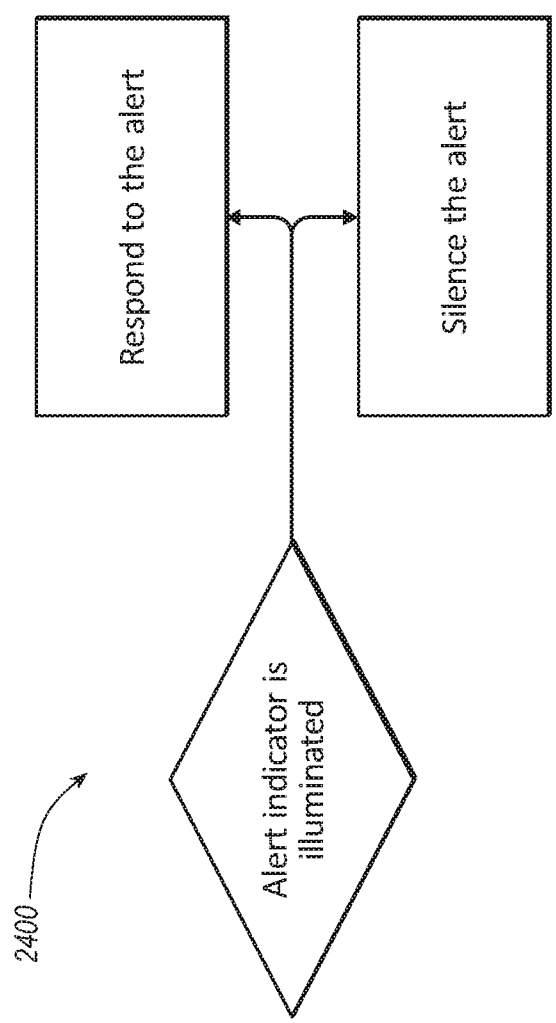
FIG. 24 illustrates a method for responding to an alert while monitoring urine output of a patient using an automated urine-output-measurement system in accordance with some embodiments.

FIG. 24 illustrates a method 2400 for responding to an alert while monitoring urine output of a patient using the automated urine-output-measurement system 100 in accordance with some embodiments.

As shown, the method 2400 includes a step of a clinician such as a nurse responding to the alert, for example, a visual alert in accordance with that for which the alert was generated. Alternatively, the method 2400 includes a step of the clinician suppressing the alert.

Figure 25:
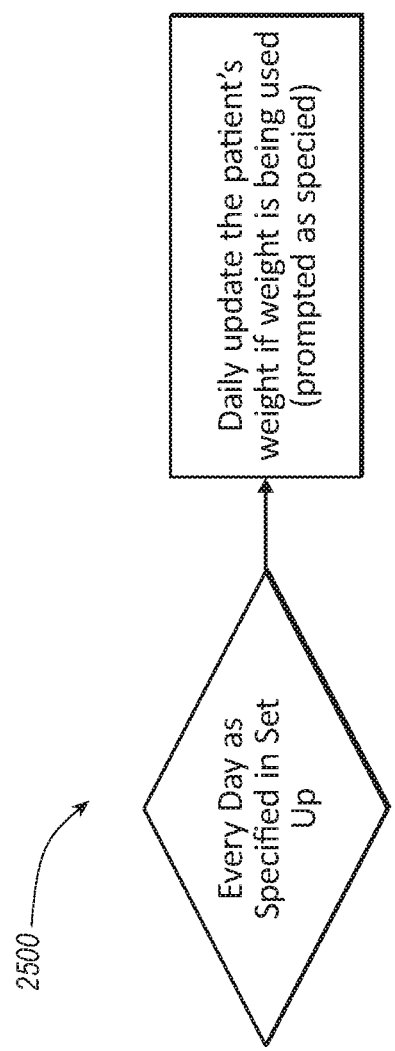
FIG. 25 illustrates a method for updating a patient information while monitoring a urine output of a patient using an automated urine-output-measurement system in accordance with some embodiments.

FIG. 25 illustrates a method 2500 for updating patient information while monitoring a urine output of a patient using the automated urine-output-measurement system 100 in accordance with some embodiments.

As shown, the method 2500 includes a step of a clinician such as a nurse updating the patient information, for example, a weight of the patient in the GUI of the integrated display screen 218 of the urine monitor 110.

Figure 26:
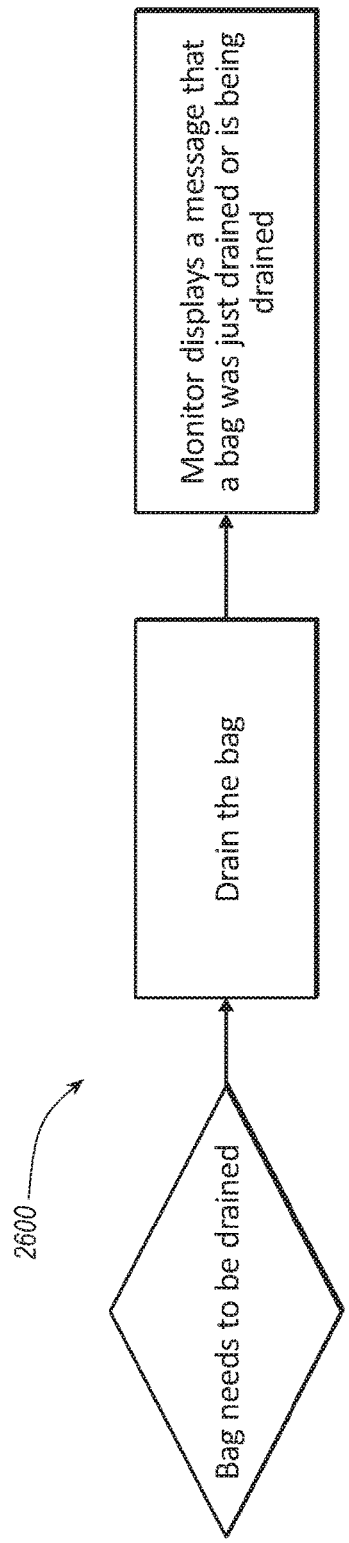
FIG. 26 illustrates a method for draining a urine-filled drainage receptacle while monitoring urine output of a patient using an automated urine-output-measurement system in accordance with some embodiments.

FIG. 26 illustrates a method 2600 for draining a urine-filled drainage receptacle 154 while monitoring urine output of a patient using the automated urine-output-measurement system 100 in accordance with some embodiments.

As shown, the method 2600 includes a step of a clinician such as a nurse draining the urine-filled drainage receptacle 154, for example, a urine-filled drainage bag when the drainage bag needs to be drained. While the clinician drains the urine-filled drainage bag, the GUI of the integrated display screen 218 of the urine monitor 110 displays a message the drainage bag is being drained in another step of the method 2600. Alternatively or additionally, the method 2600 includes a step of the GUI of the integrated display screen 218 of the urine monitor 110 displaying a message the drainage was recently drained.

Figure 27:
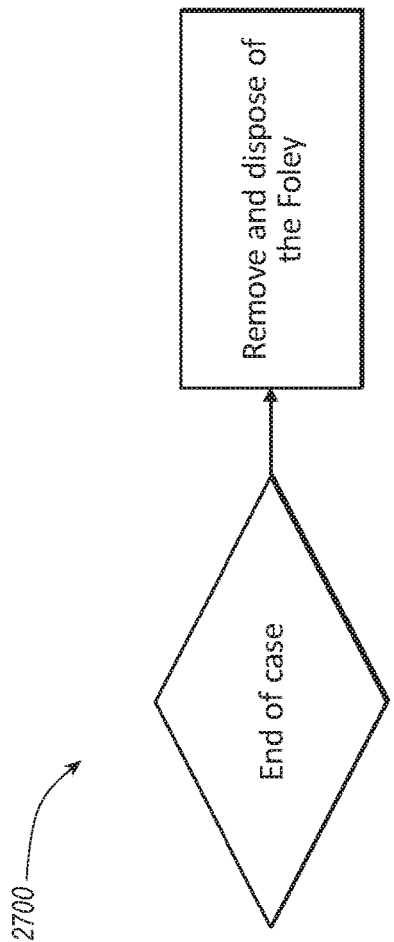
FIG. 27 illustrates a method for finalizing monitoring of urine output of a patient using an automated urine-output-measurement system in accordance with some embodiments.

FIG. 27 illustrates a method 2700 for finalizing monitoring of urine output of a patient using the automated urine-output-measurement system 100 in accordance with some embodiments.

As shown, the method 2600 includes a step of a clinician such as nurse removing the urinary catheter 140, for example, a Foley catheter from the patient and disposing the Foley catheter into an appropriate waste container for medical waste.

It should be understood that while some of the foregoing methods include an actor such as a clinician or a person such as employee of a biomedical lab, CSR, or the like, each method of such methods includes at least that clinician or employee. In other words, the clinician or employee in such methods can be more than one clinician or employee depending upon one or more circumstances. For example, the clinician or employee in such methods can be two different clinicians or employees due to a change in shifts, for example, a change in a day shift to a swing shift.

While some particular embodiments have been disclosed herein, and while the particular embodiments have been disclosed in some detail, it is not the intention for the particular embodiments to limit the scope of the concepts provided herein. Additional adaptations and/or modifications can appear to those of ordinary skill in the art, and, in broader aspects, these adaptations and/or modifications are encompassed as well. Accordingly, departures may be made from the particular embodiments disclosed herein without departing from the scope of the concepts provided herein.

What is claimed is:

1. An automated urine-output-measurement system, comprising:
   a) single-patient equipment including:
      a urinary catheter; and
      a urine-collection system including drainage tubing and a drainage receptacle; and
   b) multi-patient equipment including:
      a urine monitor including:
         a housing having a cavity configured to house an entirety of the drainage receptacle;
         a urine-measurement means for measuring urine output into the drainage receptacle; and
         an integrated display screen configured to display patient information including measurements of the urine output.

2. The automated urine-output-measurement system of claim 1, wherein the urine-measurement means is a load cell for weight-based urine-output measurements.

3. The automated urine-output-measurement system of claim 2, wherein the load cell is a tension load cell located within the housing of the urine monitor and coupled to a load-bearing hook located in a back of the cavity such that a load of the drainage receptacle is applied to the load cell while the drainage receptacle hangs from the load-bearing hook.

4. The automated urine-output-measurement system of claim 2, wherein the load cell is a compression load cell located in a bottom of the cavity such that a load of the drainage receptacle is applied to the load cell while the drainage receptacle sits on the load cell.

5. The automated urine-output-measurement system of claim 1, wherein the urine-measurement means is an in-line flow meter for volume-based urine-output measurements.

6. The automated urine-output-measurement system of claim 1, wherein the urine-measurement means is a contactless ultrasonic liquid-level sensor for volume-based urine-output measurements from above the drainage receptacle.

7. The automated urine-output-measurement system of claim 1, wherein the urine-measurement means is a contactless optical liquid-level sensor for volume-based urine-output measurements from a side of the drainage receptacle.

8. The automated urine-output-measurement system of claim 1, the urine monitor further including a radiofrequency identification ("RFID")-unit reader-writer configured to identify a presence of an RFID unit integrated into the urine-collection system, read data from the RFID unit, and write data to the RFID unit.

9. The automated urine-output-measurement system of claim 8, wherein the RFID unit is a bead around a length of the drainage tubing adjacent the drainage receptacle.

10. The automated urine-output-measurement system of claim 8, wherein the housing of the urine monitor has an RFID-unit receptacle including the RFID-unit reader-writer therein or thereabout, the RFID-unit receptacle configured to retain the drainage tubing by way of the RFID unit.

11. The automated urine-output-measurement system of claim 1, the urine monitor further including lighting features configured to indicate a state of the urine monitor, indicate positive placement of the urine-collection system or a portion thereof, illuminate the drainage receptacle, indicate a urine monitor alert, indicate a patient alert, or a combination thereof.

12. The automated urine-output-measurement system of claim 1, the urine monitor further including an embedded system including a microcontroller configured to process urine-measurement data corresponding to the urine output into the drainage receptacle, a graphics controller configured to render on the integrated display screen the patient information including the measurements of the urine output, and one or more wireless communication modules configured to wirelessly communicate the patient information including the urine output to a companion wireless device when paired therewith.

13. The automated urine-output-measurement system of claim 1, the multi-patient equipment further including a companion tablet computer configured to wirelessly communicate with the urine monitor and one or more networked computers to update electronic medical records with the patient information including the urine output or retrieve historical patient information from the electronic medical records.

14. The automated urine-output-measurement system of claim 1, the multi-patient equipment further including one or more rechargeable batteries configured to power the urine monitor.

15. The automated urine-output-measurement system of claim 1, the multi-patient equipment further including a pole mount, a bed-rail mount, or a floor stand, the housing of the urine monitor having mounting interfaces to support the pole mount, the bed-rail mount, and the floor stand.

16. The automated urine-output-measurement system of claim 1, the multi-patient equipment further including a urine-clearing device for clearing urine from the drainage tubing.

17. The automated urine-output-measurement system of claim 10, wherein the housing of the urine monitor further includes a transverse drainage-tubing channel including the RFID-unit receptacle, the transverse drainage-tubing channel configured to accommodate the drainage tubing on each side of the RFID unit when the RFID unit is around a length of the drainage tubing adjacent the drainage receptacle, as well as provide strain relief to the drainage tubing by guiding and supporting the drainage tubing to prevent kinks therein.

18. The automated urine-output-measurement system of claim 8, wherein the housing of the urine monitor further includes a longitudinal drainage-tubing channel configured to retain the drainage tubing by a compressive force on sides of the urine monitor between the RFID unit and either a backup or faux RFID unit around opposing portions of a length of the drainage tubing.

19. The automated urine-output-measurement system of claim 18, wherein the RFID-unit reader-writer is disposed within the housing on a side of the urine monitor or the urine monitor includes two RFID-unit reader-writers disposed within the housing on both sides of the urine monitor about the drainage-tubing channel.

20. The automated urine-output-measurement system of claim 18, wherein the housing of the urine monitor further includes a companion drainage-tubing slot to the transverse drainage-tubing channel, the companion drainage-tubing slot configured to accommodate the drainage tubing, as well as provide strain relief to the drainage tubing by guiding and supporting the drainage tubing to prevent kinks therein.

\* \* \* \* \*